US007110583B2

(12) United States Patent
Yamauchi

(10) Patent No.: US 7,110,583 B2
(45) Date of Patent: Sep. 19, 2006

(54) ULTRASONIC DIAGNOSTIC DEVICE AND IMAGE PROCESSING DEVICE

(75) Inventor: Masaki Yamauchi, Kadoma (JP)

(73) Assignee: Matsushita Electric Industrial, Co., Ltd., Osaka (JP)

( * ) Notice: Subject to any disclaimer, the term of this patent is extended or adjusted under 35 U.S.C. 154(b) by 1000 days.

(21) Appl. No.: 10/058,316

(22) Filed: Jan. 30, 2002

(65) Prior Publication Data
US 2002/0102023 A1 Aug. 1, 2002

(30) Foreign Application Priority Data
Jan. 31, 2001 (JP) ............................. 2001-023819

(51) Int. Cl.
G06K 9/00 (2006.01)
(52) U.S. Cl. ...................... 382/128; 382/199; 382/154; 128/915; 128/916; 600/447
(58) Field of Classification Search ................ 382/128, 382/130, 131; 128/915, 916; 600/447
See application file for complete search history.

(56) References Cited

U.S. PATENT DOCUMENTS

| 5,570,430 | A | * | 10/1996 | Sheehan et al. ............. 382/128 |
| 5,605,155 | A | * | 2/1997 | Chalana et al. ............. 600/443 |
| 5,797,844 | A | * | 8/1998 | Yoshioka et al. ............ 600/442 |
| 5,871,019 | A | * | 2/1999 | Belohlavek ................. 600/450 |
| 6,139,496 | A | * | 10/2000 | Chen et al. .................. 600/437 |
| 6,217,520 | B1 | * | 4/2001 | He et al. ..................... 600/467 |
| 6,381,350 | B1 | * | 4/2002 | Klingensmith et al. ..... 382/128 |
| 6,385,332 | B1 | * | 5/2002 | Zahalka et al. ............. 382/128 |
| 6,447,453 | B1 | * | 9/2002 | Roundhill et al. .......... 600/443 |
| 6,458,081 | B1 | * | 10/2002 | Matsui et al. ............... 600/437 |
| 6,621,924 | B1 | * | 9/2003 | Ogino et al. ................ 382/165 |
| 6,785,409 | B1 | * | 8/2004 | Suri ........................... 382/128 |

FOREIGN PATENT DOCUMENTS

| JP | 9-84793 | 3/1997 |
| JP | 2768627 | 4/1998 |
| JP | 2825358 | 9/1998 |
| JP | 11-164834 | 6/1999 |

OTHER PUBLICATIONS

Baxes, Gregory, Digital Image Processing: Principles and Applications, John Wiley & Sons, New York, 1994.*
Castleman, Kenneth, Digital Image Processing, Prentice Hall, New Jersey, 1996.*
Halit, Mehdi, et al., "PCA-Based Active Contour Model for Detection and Tracking of the Left Ventricle in Apical Echocardiographic Sequences," SPIE Conference on Applications of Digital Image Processing XXI, San Diego, CA, Jul. 1998, pp. 872-878.*

* cited by examiner

Primary Examiner—Bhavesh M. Mehta
Assistant Examiner—John Strege
(74) Attorney, Agent, or Firm—Wenderoth, Lind & Ponack, L.L.P.

(57) ABSTRACT

An ultrasonic diagnostic device includes an automatic contour extracting unit that contains an initial contour extracting unit for roughly extracting an initial contour of an object to be examined from an ultrasound image by performing a predetermined operation (such as equalization, binarization, and degeneration) on the ultrasound image. The automatic contour extracting unit also contains a dynamic contour extracting unit for accurately extracting a final contour of the object by using the extracted initial contour as an initial value and by applying an active contour model, such as the SNAKES model, to the object within the ultrasound image.

9 Claims, 30 Drawing Sheets

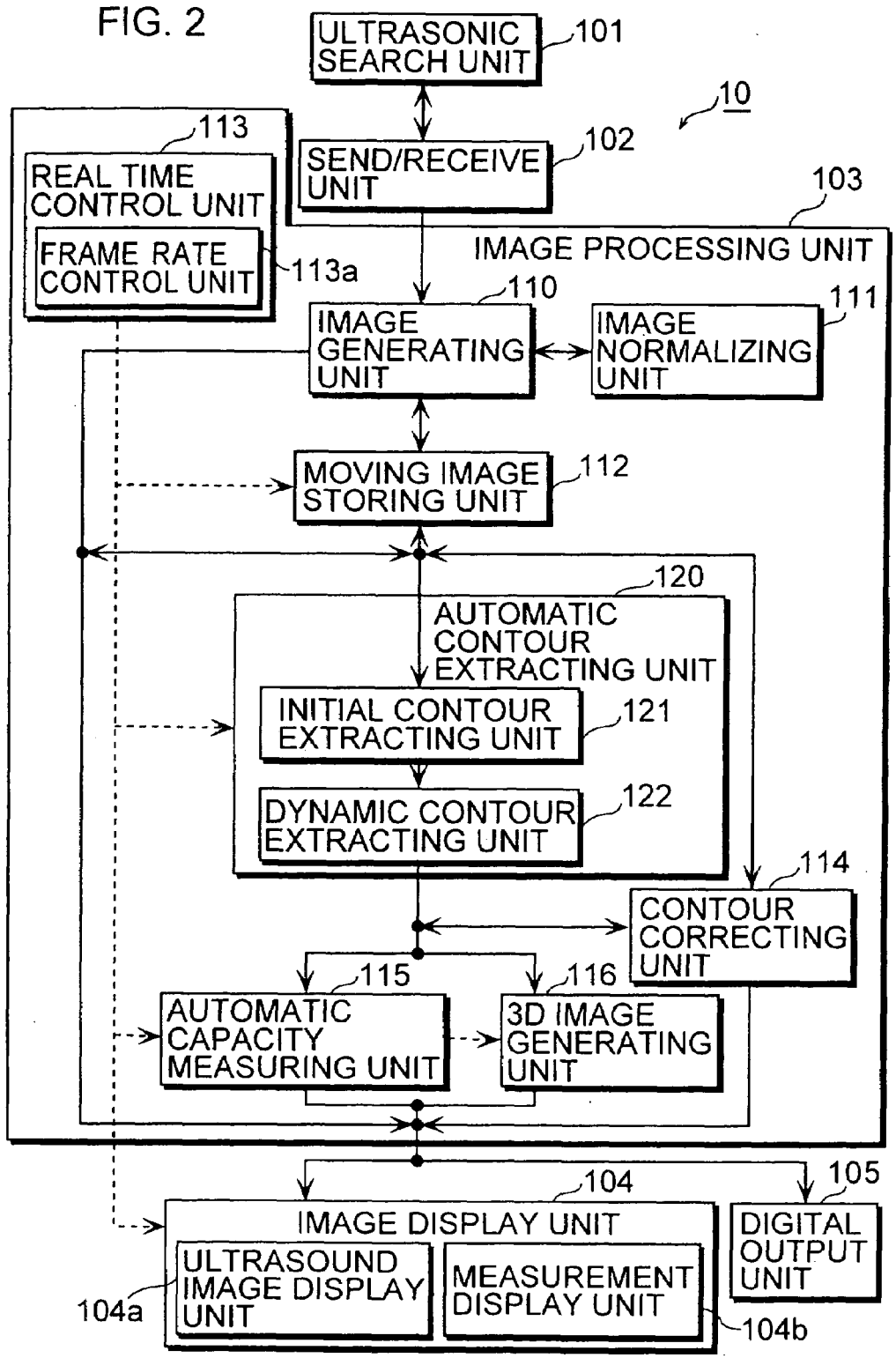

TWO
CHAMBER
VIEW

FOUR
CHAMBER
VIEW

FIG. 4
SINGLE PLANE AREA LENGTH METHOD
MAJOR AXIS "h", CROSS-SECTIONAL AREA "A"
VOLUME "V" = $8A^2/3\pi h$
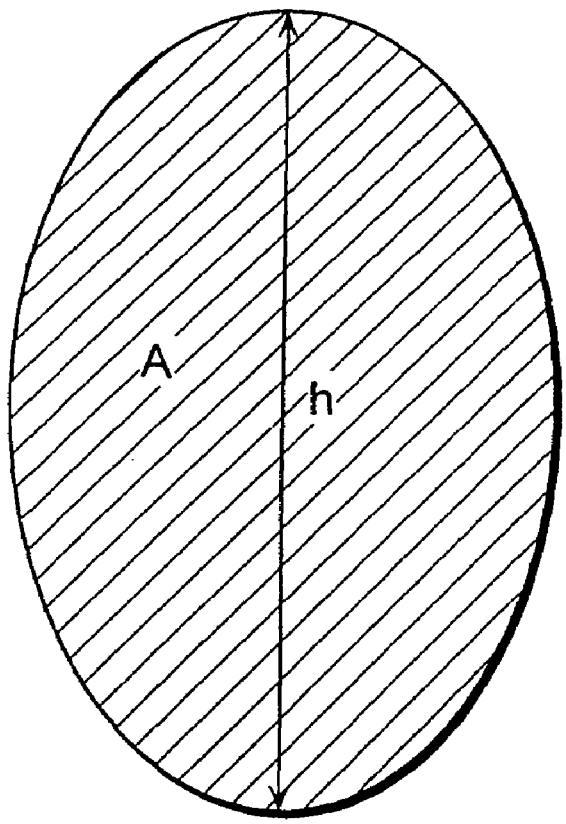

FIG. 6A EQUALIZATION
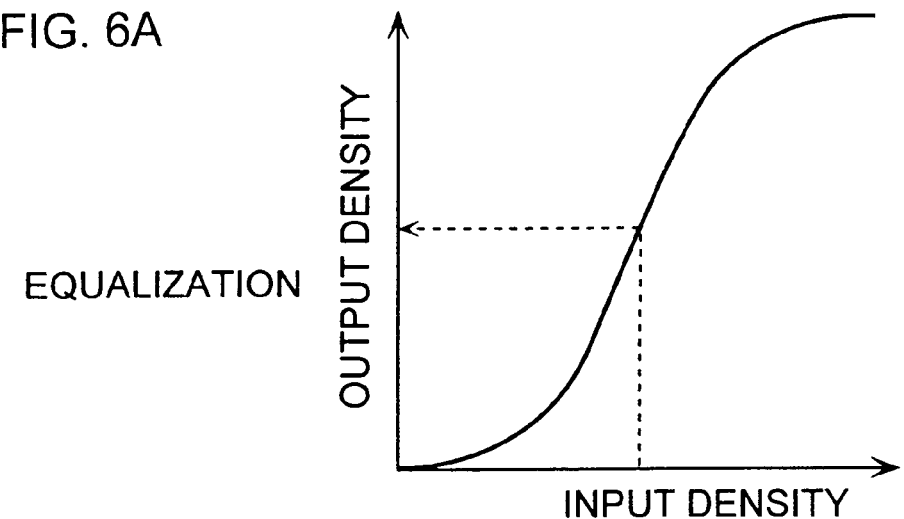
FIG. 6B
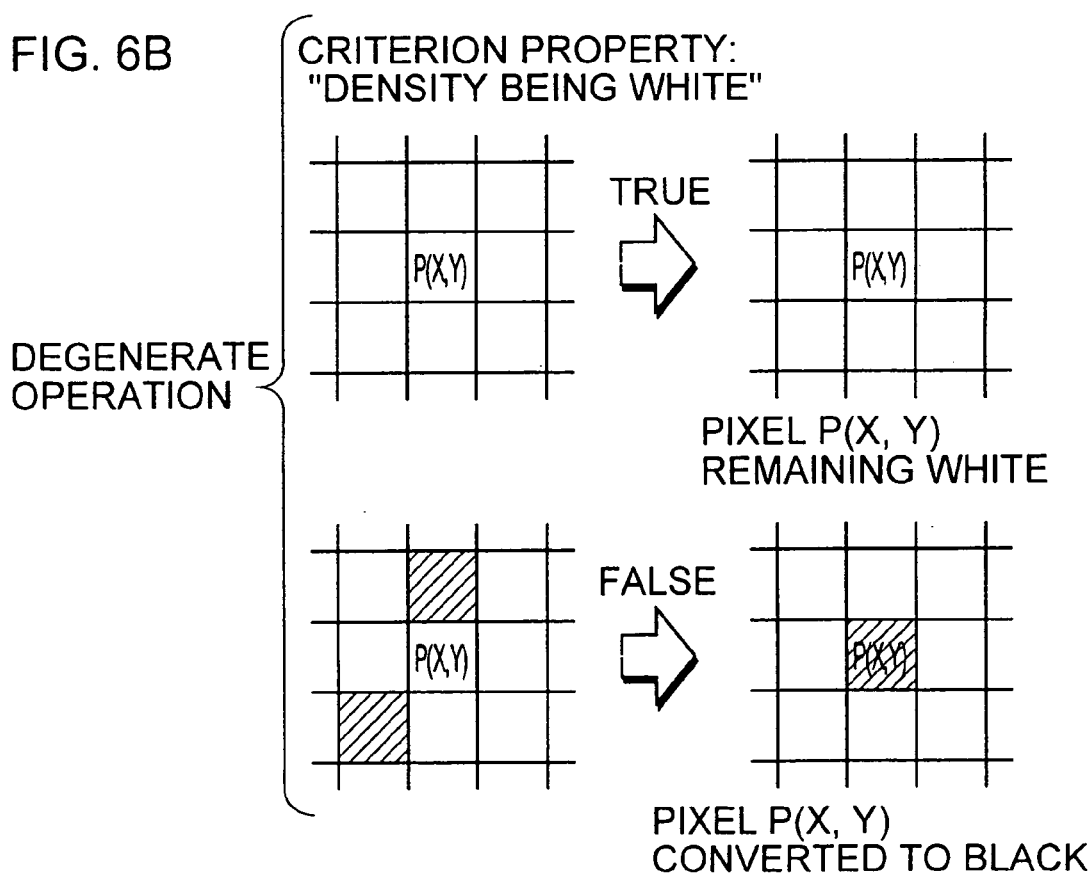

BEFORE EQUALIZATION

AFTER EQUALIZATION

AFTER BINARIZATION
CONVERSION

AFTER DEGENERATE
OPERATION

FIG. 8A
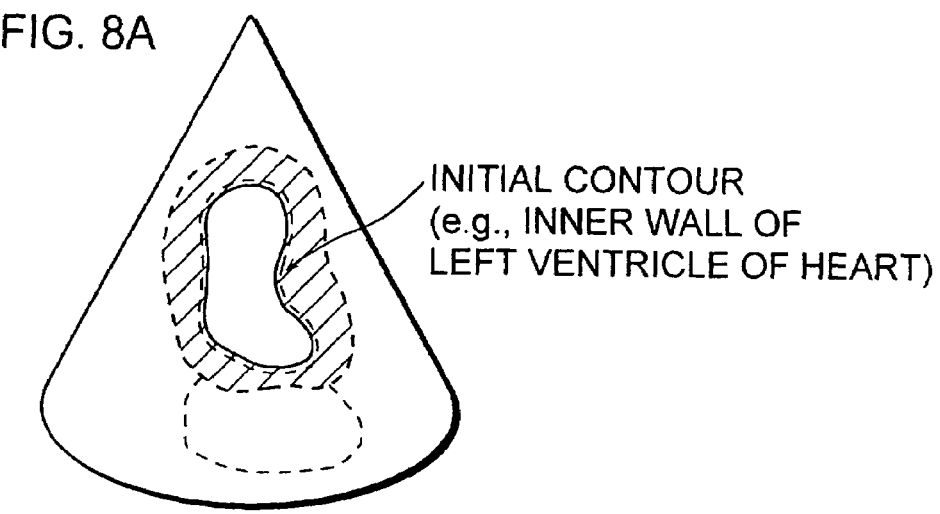
INITIAL CONTOUR
(e.g., INNER WALL OF
LEFT VENTRICLE OF HEART)
FIG. 8B1    FIG. 8B2    FIG. 8B3    FIG. 8B4
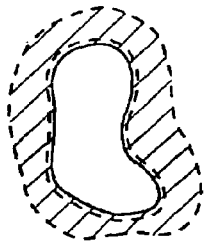 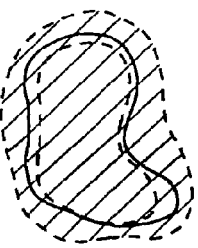 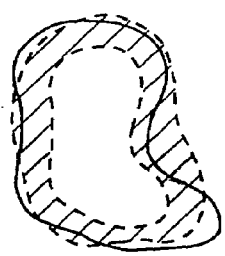 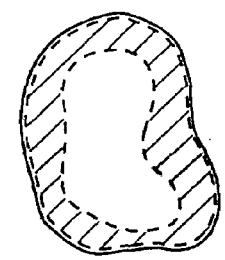

CONTOUR A

CONTOUR B

FIG. 14
BIPLANE AREA LENGTH METHOD
MAJOR AXES h1 AND h2, OF WHICH LONGER ONE IS h.
CROSS-SECTIONAL AREAS A1 AND A2
VOLUME $V = 8A_1 A_2 / 3\pi h$
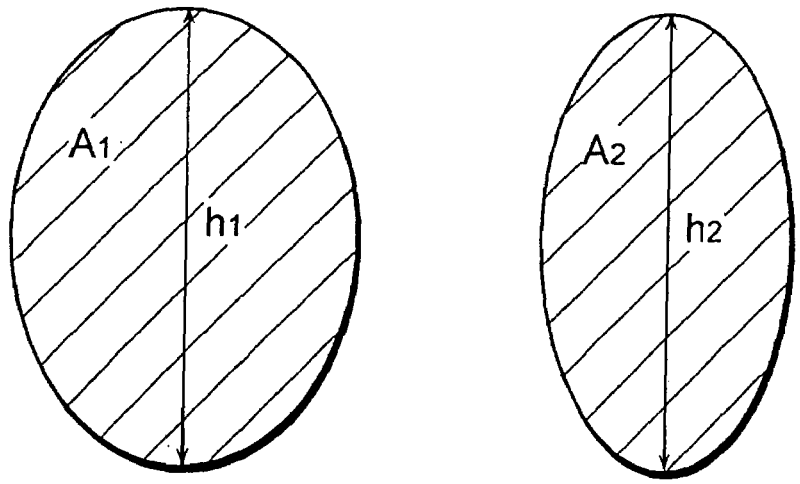
SECTIONS THAT SHARE SAME
AXIS AND ARE ORTHOGONAL TO EACH OTHER

EXTRACTION RESULT A

EXTRACTION RESULT C

EXAMPLE OF INITIAL CONTOUR SETTING BY INTERPOLATION

EXTRACTION RESULT A

EXTRACTION RESULT C

EXAMPLE OF INITIAL CONTOUR SETTING BY
BINARIZATION CONVERSION/OR-OPERATION

EXTRACTION RESULT A

EXTRACTION RESULT C

EXAMPLE OF INITIAL CONTOUR SETTING BY BINARIZATION CONVERSION/AND-OPERATION

SIMPSON METHOD

RADIUS Ai (OR CROSS-SECTIONAL AREA Si) OF EACH SLICE

INTERVAL h BETWEEN TWO SLICES

⇩

VOLUME $V = \Sigma Si \times h$
$= \Sigma (\pi \times Ai^2/4) \times h$

MODIFIED SIMPSON METHOD

EACH RADIUS Ai/Bi OF TWO CROSS SECTIONS
THAT ARE ORTHOGONAL TO EACH OTHER
INTERVAL "h" BETWEEN SLICES

⇩

VOLUME "V" = $\Sigma A_i B_i \times h \pi$

CROSS SECTIONS THAT SHARE SAME
AXIS "ℓ" AND ARE ORTHOGONAL TO EACH OTHER

ULTRASONIC DIAGNOSTIC DEVICE AND IMAGE PROCESSING DEVICE

BACKGROUND OF THE INVENTION (1) Field of the Invention

The present invention relates to an ultrasonic diagnostic device and an image processing device, and particularly to a technique to extract a contour of an object that is subject to an examination from an image.

(2) Description of Prior Art

An ultrasonic diagnostic device receives an echo which is obtained when ultrasound emitted from an ultrasonic probe is partially reflected on reflection points and surfaces of tissue of an object of a living body that is subject to an examination. The ultrasonic diagnostic device then performs signal processing for the received echo, and generates an ultrasound image (an echo image) for the examined object. Since the ultrasonic diagnostic device generates a two-dimensional (2D) ultrasound image of an examined object of a soft part and the like without invasion, the ultrasonic device is widely used as a device which offers a high level of safety and is essential in fields such as clinical medicine.

As ultrasonic diagnostic devices are increasingly in widespread use and digitized, calculating a quantitative size, such as an area, a volume, and a change in quantity, concerning a fetus, an internal organ, and a circulatory organ has become highly important as a part of screening by the use of an ultrasonic diagnostic device. For such quantitative analysis, it is necessary to accurately extract a contour (i.e., boundary) of an object to be examined, and a variety of techniques have been developed to achieve such extraction.

For instance, Japanese Laid-Open Patent Application No. H11-164834 discloses an ultrasonic image diagnostic device, for which an operator roughly traces a boundary of tissue subject to examination so that the boundary is extracted without the effects of noise.

Japanese Laid-Open Patent Application No. H09-84739 discloses an ultrasonic image processing device. This image processing device refers to textures of images, and tissue to be examined and another tissue around the tissue to be examined are analyzed by using a plurality of learning windows. Based on difference in characteristic quantity distribution between the two pieces of tissues, a boundary of the tissue subject to the examination is extracted.

Japanese Laid-Open Patent Application No. H07-246207 also discloses an ultrasonic image processing device, which extracts a contour of tissue in accordance with a plurality of sample points that are set on a boundary of the tissue.

Japanese Laid-Open Patent Application No. H04-279156 discloses an ultrasonic three-dimensional (3D) image displaying device. This 3D image displaying device compares predetermined conditions and threshold values set by an operator with those of echo data representing shades of an image, and extracts echo data corresponding to a surface of an object to be examined.

The above conventional techniques, however, have a drawback in that they require an operator to perform a number of operations and instructions, or they cannot perform a sufficiently accurate extraction of a contour of an object.

More specifically, the above ultrasonic image diagnostic device disclosed by Japanese Patent Application No. H11-164834 first requires the operator to input a guide boundary by roughly tracing tissue subject to examination with a mouse. Secondly, the operator needs to set a starting point that is used for extracting the boundary. From this starting point, scanning lines radially extend. Then the operator also needs to manually set a detection region whose center is an intersection point of each scanning line and the boundary. After this, the image diagnostic device processes ultrasound image data within the detection region to convert it into a binary ultrasound image, and detects a boundary position for which correction is necessary. The operator is then required again to manually set the boundary.

The above ultrasonic image processing device of Japanese Patent Application No. H09-84739 requires the operator to designate each learning window with a mouse or the like. The operator needs to perform this window setting while checking learning effects, and so this is an intricate operation. Moreover, the operator needs to pay close attention to selections of the learning window's position and size so as to allow the learning process to be effectively performed.

For the conventional ultrasonic image processing device of Japanese Patent Application No. H07-246207, the operator needs to set a plurality of sample points on a boundary of an object such as a tissue to be examined. A contour obtained under this method significantly varies according to which sample points are selected, and therefore setting such accurate sample points requires as much labor and time as is required to manually trace a contour. In addition, when calculations are repeatedly performed on the same image data, this image processing device cannot always extract the same contour without the operator selecting exactly the same sample points each time even if he has set them by taking into the account the tremendous amount of care and precision that is required by the manual tracing.

The above ultrasonic 3D image displaying device disclosed by Japanese Patent Application No. H04-279156 also requires an operator's operations such as for setting predetermined conditions and threshold values, but the image displaying device may call for less operator involvement than other techniques. This image displaying device, however, is susceptible to noise in an image because it extracts a contour by simply converting density information for an ultrasound image into a binary representation. This may result in extracting an incorrect contour of tissue and a part that is subject to examination.

SUMMARY OF THE INVENTION

The present invention is made in view of the above problems. Accordingly, an object of the present invention is to provide an ultrasonic diagnostic device and an image processing device that are capable of extracting a contour of an object to be examined from an ultrasound image with high accuracy without requiring the operator to perform many operations.

The above object can be achieved by an ultrasonic diagnostic device that generates and displays an ultrasound image containing an object which is subject to examination in accordance with reflection of ultrasound. This ultrasonic diagnostic device includes an automatic contour extracting unit for extracting a contour of the object from the ultrasound image by performing a predetermined operation on the ultrasound image.

With this construction, the contour of the object is extracted from the ultrasound image by using the ultrasound image itself. As a result, the operator does not need to perform troublesome input operations, and consistent stable extraction results can be always obtained.

Here, the above diagnostic ultrasonic device may also include a 3D image generating unit for accumulating each generated contour to generate and display a 3D image for the object.

This construction allows the operator to intuitively recognize the object in 3D and helps the operator to perform a precise examination.

Here, the above ultrasonic diagnostic device may also include a contour correcting unit for correcting the contour extracted by the automatic contour extracting unit in accordance with either dialog (interaction) with the operator or a standard that the contour correcting unit stores.

With this construction, the operator's abundant knowledge and experience can be reflected in the diagnostic result, so that the contour can be obtained with increased accuracy.

Here, the ultrasonic diagnostic device may further include an automatic capacity calculating unit for calculating a capacity of the object by using the extracted contour.

As a result, the operator can obtain the capacity of the object as well as its contour, which makes it possible to perform a precise examination of cavities, for instance, inside the living body.

Here, the ultrasonic diagnostic device may further include a use ascertaining unit for determining, for one of the extracted contour and the corrected contour, whether the contour is used for a subsequent operation in accordance with dialog with the operator.

For this construction, objects to be examined can be limited, and unnecessary examination, such as that for a virtual image, can be prevented from being conducted.

Here, the ultrasonic diagnostic device may further include an image normalizing unit for normalizing the ultrasound image by converting the density of pixels of the ultrasound image in such a way as to make a density distribution of the ultrasound image satisfy a predetermined condition, and the automatic contour extracting unit may perform the predetermined operation on the normalized ultrasound image to extract the contour.

This construction allows a density distribution of the ultrasound image to be narrowed to a certain range in the initial processing stage so that subsequent operations such as contour extraction can be performed not only with stability and with improved accuracy but also at a higher speed.

Here, for performing the predetermined operation, the automatic contour extracting unit may include: an initial contour extracting unit for roughly extracting an initial contour of the object; and a dynamic contour extracting unit for accurately extracting a final contour by using the extracted initial contour as an initial value and by applying an active contour model to the object within the ultrasound image.

For this construction, the initial contour is automatically and periodically extracted from the ultrasound image by using this ultrasound image itself so as to be used for the subsequent dynamic extraction. Consequently, the operator no longer needs to input an initial contour. At the same time, since consistent initial contours are automatically generated, parameters which are used for the dynamic extraction can be tuned in advance, so that a time taken by the dynamic extraction can be reduced, and the dynamic extraction can be performed with enhanced accuracy.

Here, the automatic contour extracting unit may also include an initial contour correcting unit for judging whether or not the extracted initial contour meets a predetermined standard and for correcting the initial contour when the initial contour correcting unit judges that the initial contour does not meet the predetermined standard. Furthermore, the dynamic contour extracting unit may extract the final contour by using the corrected initial contour as an initial value.

For this construction, the final contour can be dynamically extracted by using the more accurate initial contour, so that a total time taken to extract the contour can be reduced.

Here, the automatic contour extracting unit may also include an initial contour selecting unit for storing a criterion in advance and selecting an initial contour meeting the criterion from a plurality of extracted initial contours when the initial contour extracting unit extracts the plurality of initial contours. The dynamic contour extracting unit may extract the final contour by using the selected initial contour as an initial value.

With this construction, initial contours of objects that meet the criterion and that should be examined are only selected from the plurality of initial contours which have been extracted. This prevents an unnecessary examination from being conducted for objects that are not the subject of examination and thereby cuts unnecessary examination time.

Here, when a plurality of extracted initial contours meet the stored criterion, the initial contour selecting unit may select the plurality of extracted initial contours.

This construction allows an examination to be performed for the plurality of objects in parallel, and therefore reduces overall time taken by examination.

Here, the automatic contour extracting unit may also include an external selection unit for selecting at least one initial contour from a plurality of initial contours in accordance with dialog with an operator when the initial contour extracting unit extracts the plurality of initial contours. The dynamic contour extracting unit may extract a final contour in accordance with the at least one selected initial contour as an initial value.

With this construction, an examination can be performed while limiting its target objects to those that are desired by the operator.

Here, the normalizing unit may include a condition storing unit for storing the predetermined condition in advance; a density converting unit for converting the density of the pixels by using a plurality of transform functions to generate a plurality of ultrasound images; and a control judging unit for specifying, out of the plurality of ultrasound images, an ultrasound image that satisfies the stored predetermined condition, and outputting the specified ultrasound image as a normalized ultrasound image.

This construction ensures that a normalization which is suitable for a type of a target object is performed on an ultrasound image containing the object through uniform operation.

Here, the automatic contour extracting unit may also include an initial contour input unit for obtaining an initial contour that roughly specifies the object in accordance with dialog with an operator. The dynamic contour extracting unit may extract a final contour by using the obtained initial contour as an initial value. The automatic contour extracting unit may also include a contour selecting unit for selecting one of the initial contour obtained by the initial contour input unit and the initial contour extracted by the initial contour extracting unit. The dynamic contour extracting unit may extract a final contour by using the selected initial contour as an initial value.

For this construction, the initial contour is extracted either automatically or in accordance with the operator's designation, and therefore the operator's intention can be reflected in the contour extraction.

Here, the automatic contour extracting unit may extract a contour of a left ventricle of a heart as the final contour, and the automatic capacity calculating unit may calculate a capacity of the left ventricle. The ultrasonic diagnostic device may further include a measurement display unit for displaying the calculated capacity. The ultrasonic diagnostic device may further include a real time control unit for having an operation repeatedly performed at a fixed frame rate, where this operation includes: (a) the extraction of the final contour by the automatic contour extracting unit; (b) the calculation of the capacity; and (c) the display of the calculated capacity.

This construction achieves an ultrasonic diagnostic device which is capable of high-speed accurate examination dedicated to the heart.

Here, the ultrasonic diagnostic device may further include an image display unit for displaying at least one of the ultrasound image and the final contour. The real time control unit may control the image display unit and the measurement display unit so that the calculated capacity is displayed in synchronization with the display of the at least one of the ultrasound image and the final contour.

For this construction, the operator can view changes in the contour of the heart and its capacity in real time and thus perform examination of the heart with improved accuracy.

Here, the automatic contour extracting unit may extract a final contour from each of two ultrasound images corresponding to two cross sections that are orthogonal to each other. The capacity calculating unit may use each extracted final contour in an approximate expression to calculate a capacity, where the approximate expression is pursuant to one of a modified Simpson method and a biplane area length method.

For this construction, the capacity of the left ventricle of the heart is calculated in accordance with two approximate expressions that use values which are related to two different cross sections of the left ventricle. As a result, a more accurate capacity value can be obtained.

Here, the ultrasonic diagnostic device may further include: a real time control unit for having an operation repeatedly performed at a fixed frame rate, where the operation includes (a) generation of the ultrasound image, (b) the extraction of the final contour by the automatic contour extracting unit, and (c) the calculation of the capacity; and a moving image storing unit for accumulating ultrasound images that are generated through the repeatedly performed operation to generate and store moving images for the object. For this construction, the ultrasound images and contours obtained in real time can be accumulated to be precisely analyzed later as in a close examination.

Here, the ultrasonic diagnostic device may further include a real time control unit for having an operation repeatedly performed at a fixed frame rate, where the operation includes: (a) generation of the ultrasound image; (b) the extraction of the final contour by the automatic contour extracting unit; and (c) the calculation of the capacity. The real time control unit may include a frame rate control unit for monitoring the operation and changing the frame rate to have the operation be completely performed.

This construction can prevent malfunctions resulting from an uncompleted analysis, and partial loss of an ultrasound image due to a shortage of storage areas when the frame rate is extremely high, or when an ultrasound image incurring a huge operational load is suddenly generated.

Here, the automatic contour extracting unit may extract the contour by using previously extracted contours.

This construction reduces a time taken for the extraction of the initial contour and allows the initial contour to be extracted with increased accuracy.

The present invention can also be achieved as an image processing device that includes the above automatic contour extracting unit, and as a program to be executed by a general-purpose computer to perform functions of the automatic contour extracting unit.

As has been described, the ultrasonic diagnostic device and the image processing device of the present invention are capable of automatically extracting a contour of an object to be examined with high accuracy and stability. This not only reduces operational load of doctors but also improves the quality of medical care and thereby reduces national medical costs. The present invention therefore has great value in its practicality.

BRIEF DESCRIPTION OF THE DRAWINGS

These and the other objects, advantages and features of the present invention will become more apparent from the following detailed description when taken in conjunction with the accompanying drawings which illustrate specific embodiments of the invention.

In the drawings:

FIG. 2 is a block diagram showing a main function configuration of the ultrasonic diagnostic device;

FIG. 4 is a diagram used to explain a method (the single plane area length method) used by an automatic capacity measuring unit of the ultrasonic diagnostic device for calculating a capacity;

FIG. 6A shows an example of a conversion curve of density equalization performed by a density adjusting unit contained in the initial contour extracting unit;

FIG. 6B is a diagram used to explain a degenerate operation performed by a degenerating unit contained in the initial contour extracting unit;

FIG. 8A shows an example of an initial contour, which is extracted by the initial contour extracting unit, of a left ventricle of a heart;

FIGS. 8B1–8B4 show states in which extracted contours of the left ventricle gradually become accurate through dynamic extraction that uses the extracted initial contour;

FIG. 14 is a diagram used to explain a method (single biplane area length method) used by an automatic capacity measuring unit of the ultrasonic diagnostic device for calculating a capacity;

DETAILED DESCRIPTION OF THE PREFERRED EMBODIMENTS

The following describes the present invention based on several embodiments and the drawings.

First Embodiment

Figure 1:
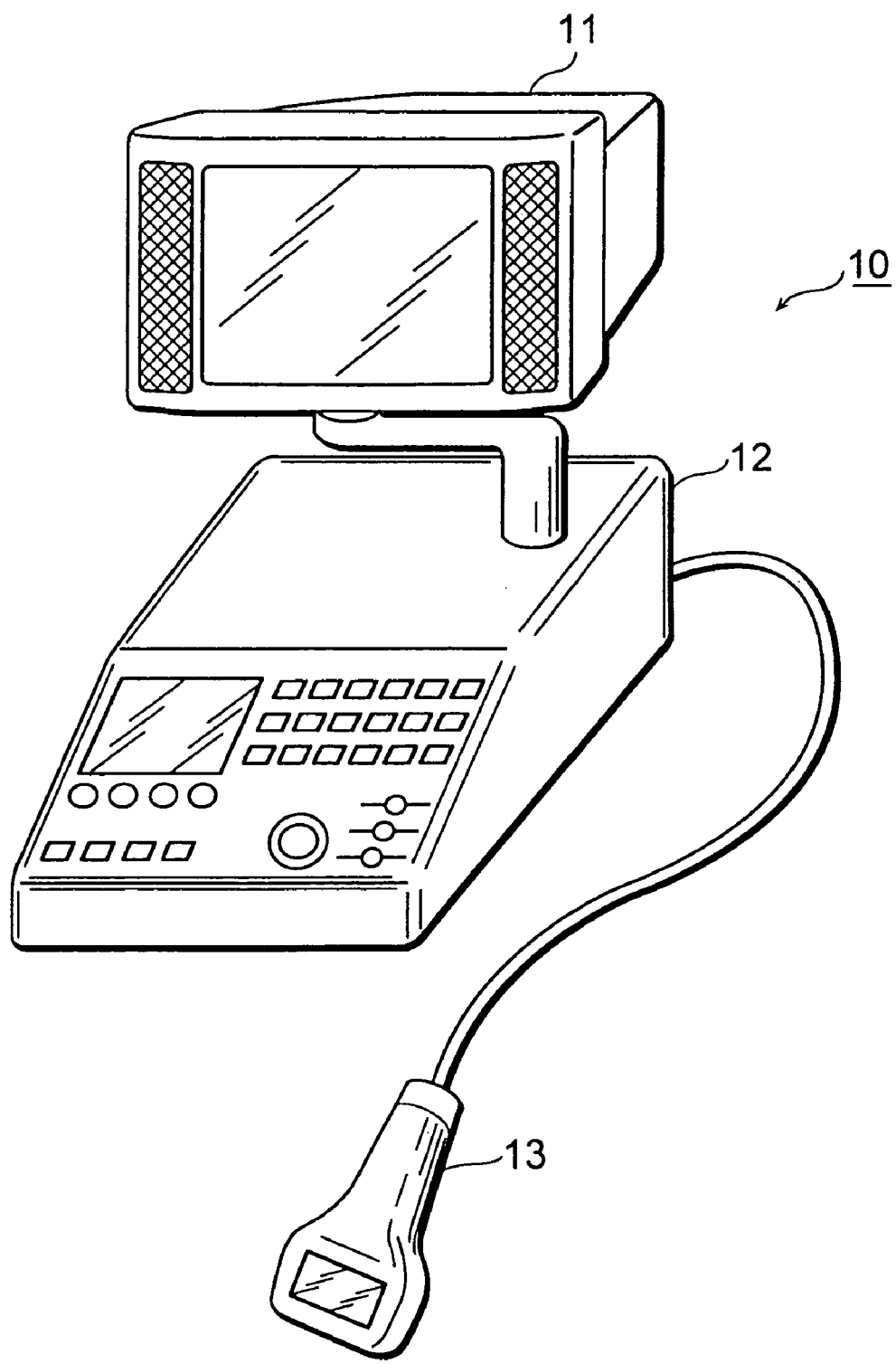
FIG. 1 shows an external view of an ultrasonic diagnostic device according to the first embodiment of the present invention.

FIG. 1 shows an external view of a digital ultrasonic diagnostic device 10 according to the first embodiment of the present invention. This ultrasonic diagnostic device 10 not only generates ultrasound images of a fetus, an internal organ, a heart, and the like according to an echo method, but also automatically extracts a contour of an object of interest, such as cancerous tissue and an inner wall of a heart in a fetus and an internal organ. The ultrasonic diagnostic device 10 also calculates a capacity of this object and generates its 3D image in real time. The ultrasonic diagnostic device 10 includes, as its major hardware, a display apparatus 11, a main unit 12, and a probe 13.

The display apparatus 11 is a cathode-ray tube (CRT) or the like, whose front is covered by a transparent touchscreen panel. The display apparatus 11 displays the generated ultrasound image, contour, and measurement result in gray scale or color, and also receives instructions related to the generated image from an operator via a stylus and the like.

The probe 13 is a search unit containing an ultrasonic oscillator and an acoustic lens for receiving and sending ultrasound. The probe 13 includes a liquid crystal display (LCD) unit that displays measurement values such as a capacity of the object in real time.

The main unit 12 includes the following elements: a send/receive circuit for electronic scanning with ultrasound; a signal/image processing circuit containing a digital signal processor (DSP) and a central processing unit (CPU); an operational panel containing a group of switches, a track ball, and an LCD for interface with the operator; and a mouse.

FIG. 2 is a block diagram showing a function configuration of the ultrasonic diagnostic device 10 in FIG. 1. The ultrasonic diagnostic device 10 can be roughly divided into an ultrasonic search unit 101, a send/receive unit 102, an image processing unit 103, an image display unit 104, and a digital output unit 105.

The ultrasonic search unit 101 functionally corresponds to the probe 13 in FIG. 1, and scans the object with an ultrasonic beam according to a signal from the send/receive unit 102 by using the phased array method.

The send/receive unit 102 is achieved by a sender/beam former for having the ultrasonic search unit 101 generate ultrasound, and by a receiver/beam former for converting ultrasound received by the ultrasonic search unit 101 into an electric signal and sending the electric signal to the image processing unit 103.

The image processing unit 103 processes the electric signal sent from the send/receive unit 102 in a predetermined manner to generate an ultrasound image, and automatically extracts a contour of the object of interest within the generated ultrasound image. The image processing unit 103 also performs post-processing such as a capacity calculation. The image processing unit 103 is achieved chiefly by the main unit 12 in FIG. 1, and includes an image generating unit 110, an image normalizing 111, a moving image storing unit 112, a real time control unit 113, a contour correcting unit 114, an automatic capacity measuring unit 115, a 3D image generating unit 116, and an automatic contour extracting unit 120.

The image generating unit 110 performs analog-to-digital (A/D) conversion on the electric signal sent from the send/receive unit 102 to generate an ultrasound image each time the ultrasonic search unit 101 performs one scan. The generated ultrasound image may be, for instance, an image of 256×256 pixels (with 8-bit density resolution per pixel) in gray scale.

Prior to image processing (such as a contour extracting operation), the image normalizing unit 111 normalizes the ultrasound image generated by the image generating unit 110 to set its density distribution within a predetermine range. This may be achieved, for instance, by allowing the operator to select one of the following conversion operations: keeping a dynamic range of the density distribution within a predetermined range; keeping variance of the density distribution within a predetermined value; and keeping an average value of the density distribution within a predetermined value range. The image normalizing unit 111 then performs the selected conversion operation by using a look up table (LUT), or performs the selected conversion operation only on a region of interest (ROI) containing the object within the ultrasound image. The image normalizing unit 111 also may eliminate noise from the ultrasound image such as by calculating a weighted average of the density of adjacent pixels, and remove a bias by using a band-pass filter or by subtracting a predetermined value from a density value of each pixel.

The moving image storing unit 112 is achieved by a memory, an Moving Picture Experts Group (MPEG) encoder, and the like. Whenever the image generating unit 110 and the image normalizing unit 111 generate a new (normalized) ultrasound image, the moving image storing unit 112 either stores the generated ultrasound image as it is, or compresses and encodes the ultrasound image as moving image data before storing the generated ultrasound image.

When sampling at a high frame rate is continuously performed for ultrasound images, subsequent operations may not be performed in real time (this is the case for continuous sampling performed when a function of the real time control unit 113 is off, which will be described later). For such a case, the moving image storing unit 112 temporarily stores all the image data to be later displayed and processed such as for a contour extraction, and thus functions as a data recording unit.

For instance, ordinary ultrasonic diagnostic devices now use a frame rate of 10 to 30 frames per second. In recent years, however, ultrasonic diagnostic devices are required to use 60 or more frames per second in a medical field for heart and circulatory organs. The moving image storing unit 112 is therefore useful in that it can store ultrasound images corresponding to several pulsebeats that are continuously sampled at a higher speed so that they can be later examined.

After the image generating unit 110 and the image normalizing unit 111 generate a new ultrasound image, the automatic contour extracting unit 120 automatically extracts a contour of an object to be examined, such as a heart, within the ultrasound image by performing a predetermined operation on the ultrasound image. Operations of the automatic contour extracting unit 120 can be roughly divided into the two steps, which are performed by the following two units: (1) an initial contour extracting unit 121 that extracts a rough contour of the object; and (2) a dynamic contour extracting unit 122 that extracts more accurate contour based on the rough contour by applying an active contour model to the object.

This automatic contour extracting unit 120 has the following two advantages: (1) automatically extracting the contour of the object from the ultrasound image without requiring the operator to perform an input operation; and (2) extracting the contour at a high speed with great accuracy through two-step operations that are dedicated to rough extraction and accurate extraction. Note that, as will be described later, the automatic contour extracting unit 120 does not reject an operator's input operation which specifies, for instance, an initial contour. The contour extracting unit 120 thus can also perform contour extraction in accordance with an operator's input operation.

The initial contour extracting unit 121 also includes a function for receiving feedback, that is, referring to immediately preceding contour data extracted by the dynamic contour extracting unit 122 to extract a contour from a new ultrasound image when the initial contour extracting unit 121 continuously receives new ultrasound images.

Figure 3A:
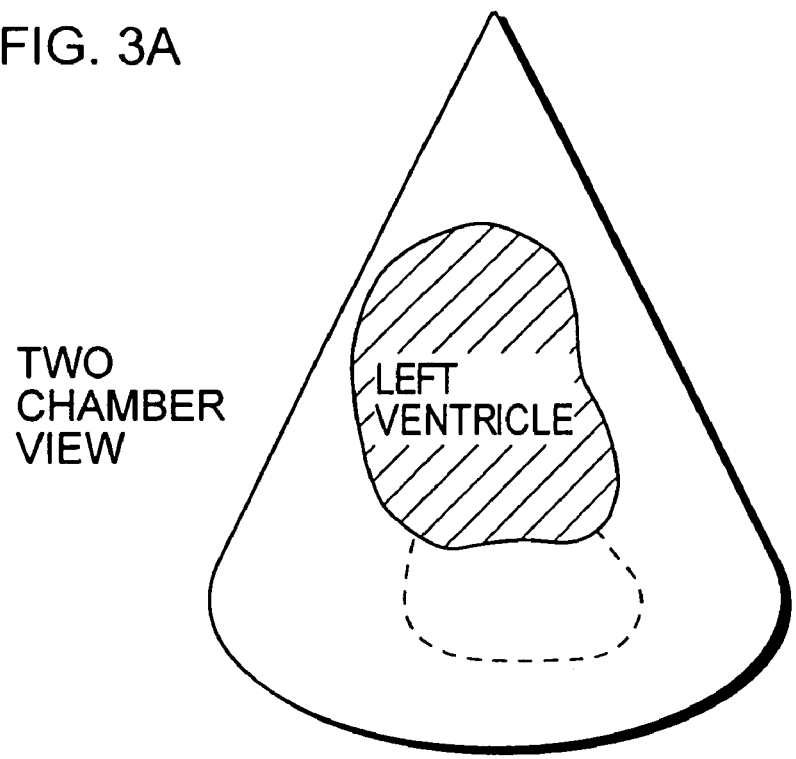
FIGS. 3A and 3B show examples of ultrasound images of a heart which are extracted by an automatic contour extracting unit of the ultrasonic diagnostic device, in a two chamber view and a four chamber view, respectively.
Figure 3B:
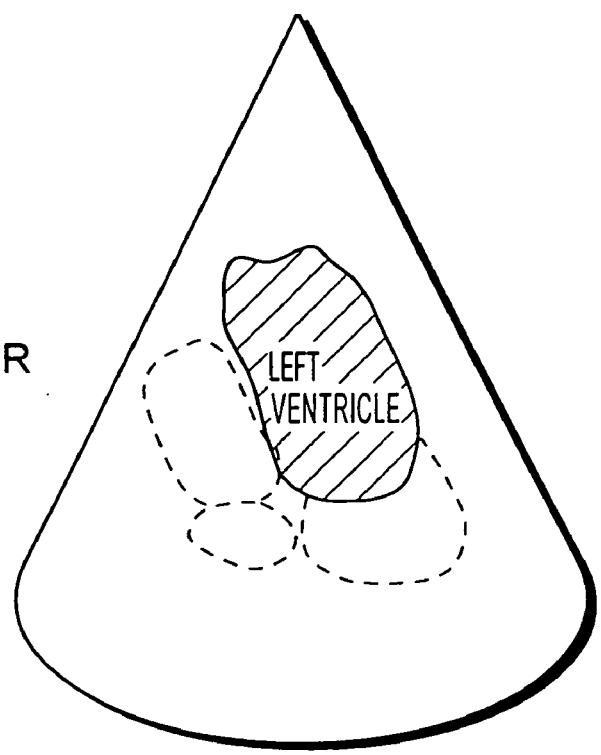

FIGS. 3A and 3B are provided to explain a function of the automatic contour extracting unit 120, and show examples of ultrasound images of a heart in a two chamber view and a four chamber view, respectively. With a left ventricle as an object of interest, the automatic contour extracting unit 120 extracts a contour (boundary, which is represented by a solid line surrounding a shaded area) of the left ventricle from the ultrasound image. This two chamber view includes a left ventricle and a left atrium, and the four chamber view includes a right ventricle and a right atrium as well as the left ventricle and the left atrium.

The contour correcting unit 114 corrects the contour extracted by the automatic contour extracting unit 120 when the extracted contour takes an abnormal shape which deviates from a predetermined standard that the contour correcting unit 114 stores. The contour correcting unit 114 may perform this correction by changing some of parameters used by the automatic contour extracting unit 120 for extracting a contour and then having the automatic contour extracting unit 120 extract the contour again.

More specifically, the contour correcting unit 114 makes the above judgment as to whether the extracted contour takes an abnormal shape which deviates from the predetermined standard by referring to a differential between the current contour and a contour in a database that was generated in the past, or to an energy value of an active contour model, which is described later. For correcting the contour, the contour correcting unit 114 first specifies, out of the database, a typical contour that is the most alike to the contour to be corrected, and then corrects data on this contour's part that significantly differs from that of the specified typical contour to make the part match the typical contour.

Following this, in accordance with an instruction set by the operator in advance, the contour correcting unit 114 sends corrected contour data to one of the automatic capacity measuring unit 115, the image display unit 104, and the automatic contour extracting unit 120 to have operations performed for the corrected contour (or a contour before correction), such as a capacity measurement, image display, and contour extraction.

The automatic capacity measuring unit 115 calculates a certain length and area related to the contour extracted by the automatic contour extracting unit 120 (or to the contour corrected by the contour correcting unit 114), and then calculates a capacity of the object of interest according to an approximate expression under the single plane area length method.

FIG. 4 is provided to explain the single plane area length method used by the automatic capacity measuring unit 115 for calculating a capacity of the object. After the automatic contour extracting unit 120 extracts the contour, the automatic capacity measuring unit 115 calculates a total number of pixels surrounded by this contour, a longest length of a coordinate axis across the contour, and other necessary values to specify a cross-sectional area "A" and a major axis "h", and calculates the capacity of the object by using the approximate expression shown in FIG. 4.

The 3D image generating unit 116 continuously receives data on the contour either extracted by the automatic contour extracting unit 120 or corrected by the contour correcting unit 114, and generates 3D image data of the object from the accumulated 2D contour data in accordance with information provided in advance, such as a moving speed of the ultrasonic search unit 101 and a scanning direction (i.e., a direction of a cross section) of ultrasound. The 3D image generating unit 116 stores the generated 3D image data.

Based on an operator's instructions provided in advance, the 3D image generating unit 116 generates 3D data incorporating either a wire frame model made up of only line data of the extracted contour, or a surface model for which the extracted contour is represented as an outer surface or an inner surface of the object. The 3D image generating unit 116 also performs volume rendering using contour data of different ultrasound images for different cross sections, and generates 3D data of the object viewed from a certain direction by using ray casting.

The real time control unit 113 includes an interrupt control circuit that repeatedly sends a trigger signal to each unit (such as the moving image storing unit 112, the automatic contour extracting unit 120, the automatic capacity measuring unit 115, the 3D image generating unit 116, and the image display unit 104). By doing so, the real time control unit 113 controls the processing of the image processing unit 103 and the image display unit 104 to have the processing repeatedly performed at a certain frame rate (30 frames per second, for instance) synchronously. The real time control unit 113 also includes a frame rate control unit 113a.

The frame rate control unit 113a monitors a processing state (or whether the processing is completed) of each unit, and the free space of an internal memory to detect an adverse state in which a predetermined level of leeway is not secured in a unit. Upon detecting such an adverse state, the frame rate control unit 113a adjusts the frame rate such as by lowering it. This can prevent malfunctions, including a partial loss of an ultrasound image and an error of not yielding a capacity measurement, which may occur when an ultrasound image incurring a huge operational load is generated suddenly, or when repeated processing is performed due to the processing of the contour correcting unit 114.

The image display unit 104 is achieved by a graphic accelerator and a scan converter, and includes the following units: an ultrasound image display unit 104a for graphically presenting images generated by the image processing unit 103, such as an ultrasound image, moving images, a contour, and a 3D image, onto the display apparatus 11 and the LCD unit of the probe 13; and a measurement display unit 104b for presenting an object's capacity (or graph related to the capacity) obtained by the automatic capacity measuring unit 115 onto the LCD units of the probe 13 and the main unit 12.

In displaying a measurement such as a capacity value and a graph, the measurement display unit 104b superimposes the measurement over an ultrasound image displayed by the ultrasound image display unit 104a (which is to say, measurement data is inserted into image data).

The digital output unit 105 is achieved by a parallel interface circuit and other elements, and outputs a digital signal representing an image or a capacity value generated by the image processing unit 103 to a device in the periphery, such as a personal computer (PC).

Each unit shown in FIG. 2 performs its processing in an operational mode (which may be mode to pause the processing) that is set by the operator before diagnosis is conducted. For instance, it is possible for the operator to prohibit (pause) processing, such as normalization by the image normalizing unit 111, moving image generation by the moving image storing unit 112, correction by the contour correcting unit 114, calculation by the automatic capacity measuring unit 115, and 3D data generation by the 3D image generating unit 116. The operator can also freely set and change a variety of parameters that are used in each processing.

The following describes the automatic contour extracting unit 120 in detail, which is a characteristic element of the above ultrasonic diagnostic device 10.

Figure 5:
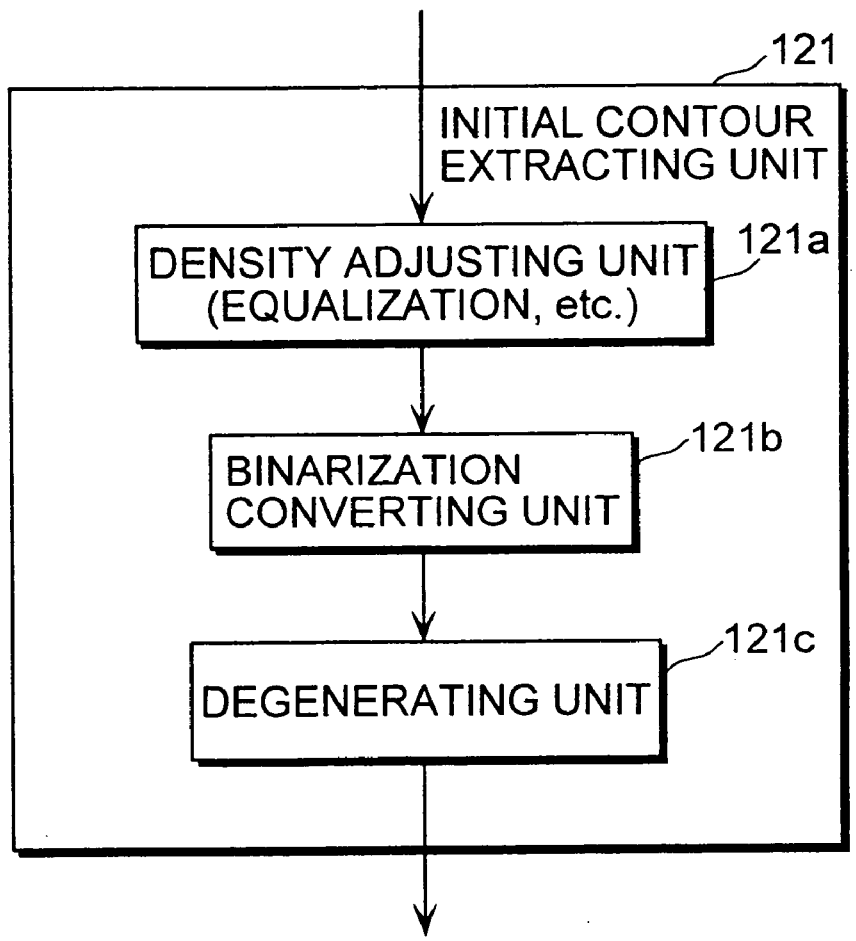
FIG. 5 is a block diagram showing a detailed function configuration of an initial contour extracting unit contained in the automatic contour extracting unit.

FIG. 5 is a block diagram showing a detailed construction of the initial contour extracting unit 121 included in the automatic contour extracting unit 120. For roughly specifying a contour of an object of interest within an ultrasound image, the initial contour extracting unit 121 includes a density adjusting unit 121a, a binarization (converting) unit 121b, and a degenerating unit 121c.

The density adjusting unit 121a changes density values of an inputted ultrasound image to facilitate the extraction of an initial contour prior to the extraction. More specifically, the density adjusting unit 121a performs, for all or designated parts of the ultrasound image, one or more operations selected out of noise removal, use of the band-pass filter, bias removal, edge enhancement, density equalization, and the like.

The edge enhancement refers to an operation for converting the density value of a pixel into, for instance, a differential value between the density of this pixel and the density of an adjacent pixel.

The density equalization refers to an operation for correcting contrast distortion (i.e., a state in which density values concentrate close to black or white) of the ultrasound image. For instance, this operation may be density conversion in accordance with a transform function (which enhances the density of halftones) held in the LUT, as shown in FIG. 6A.

The binarization unit 121b compares a density value, which is adjusted by the density adjusting unit 121a, of each pixel with a predetermined threshold value to convert the density value into one of two values, that is, a white pixel and a black pixel to generate binary image data.

The degenerating unit 121c performs a degenerate operation for the binary image data generated by the binarization unit 121b, and outputs the degenerated result as an initial contour to the dynamic contour extracting unit 122. The degenerate operation refers to an operation for outputting a signal of "TRUE" when properties (density for this embodiment) of a pixel and other pixels (e.g., eight pixels adjacent to the pixel) surrounding this pixel are the same as a property set as a criterion. On the other hand, when the above pixels include any one pixel whose property is different from the criterion property, a signal of "FALSE" is outputted. This degenerate operation is performed for the entire image data a given number of times.

For instance, assume that the criterion property for the binary image data is set as "density being white (0)" as shown in FIG. 6B. With a pixel "P" specified by coordinates (X, Y), the signal "TRUE" (or "0", for instance) is outputted when density values of this pixel P(X, Y) and adjacent eight pixels as follows are white (0): pixels of P(X−1, Y); P(X+1, Y); P(X, Y−1); P(X, Y+1); P(X−1, Y−1); P(X+1, Y−1); P(X−1, Y+1); and P(X+1, Y+1). On the other hand, the signal "FALSE" is outputted for this pixel P(X, Y) when there is any one pixel, out of the above nine pixels, that has a density value of black ("1"). This degenerate operation is performed for every pixel. When such conversion operation is repeatedly performed, a white region gradually recedes. Accordingly, this degenerate operation is stopped, for instance, when it has been performed a predetermined number of times, or when a number of target regions for degeneration (i.e., white regions for the current example) lowers to either one or a predetermine number.

Figure 7A:
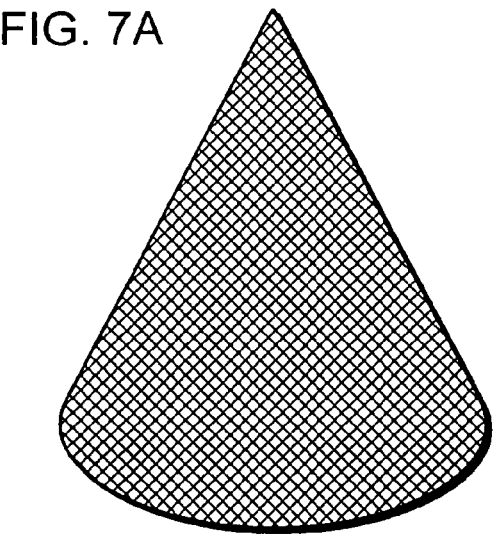
FIGS. 7A–7D show changing states of an ultrasound image obtained by an equalization, binarization, and degenerate operation which are performed by the initial contour extracting unit.
Figure 7B:
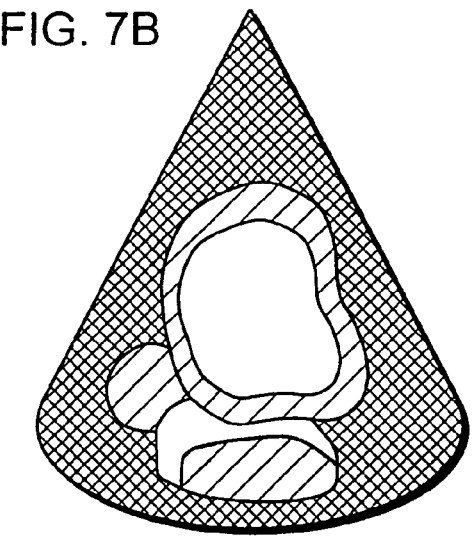
Figure 7C:
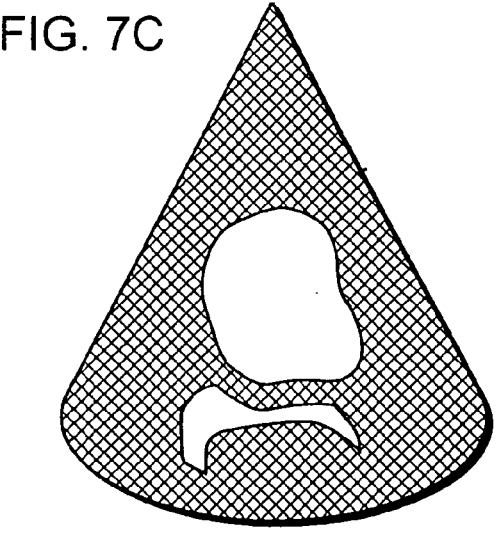
Figure 7D:
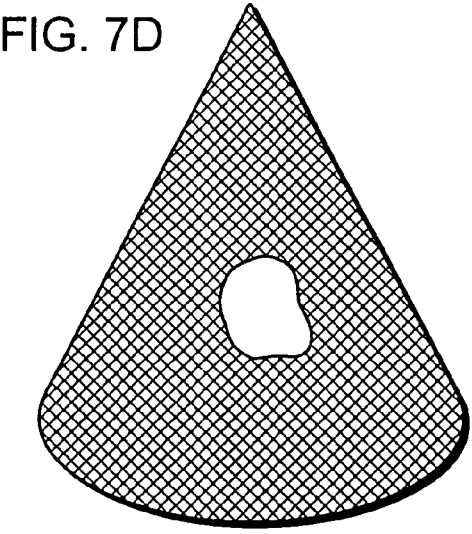

FIGS. 7A–7D show changing states of an ultrasound image on which the operations of the units 121a–121c of the initial contour extracting unit 121 shown in FIG. 5 are performed. FIG. 7A shows the ultrasound image soon after it is inputted to the initial contour extracting unit 121, and FIG. 7B shows the ultrasound image on which the density adjusting unit 121a performs density equalization. FIG. 7C shows the ultrasound image on which the binarization unit 121b performs binarization (i.e., converting non-white regions into black regions, with white regions being left as they are for this example). FIG. 7D shows the ultrasound image on which the degenerating unit 121c performs the degenerate operation, with the criterion property as "density being white" for this example.

FIGS. 8A–8B are used to explain a detailed operation of the dynamic contour extracting unit 122. FIG. 8A shows an example of an initial contour (of a left ventricle's inner wall of a heart for this example) of the object of interest (i.e., the left ventricle) inputted from the initial contour extracting unit 121 to the dynamic contour extracting unit 122. FIGS. 8B1–8B4 show states in which extracted contours of the left ventricle gradually become accurate through iterative calculations performed by the dynamic contour extracting unit 122.

The dynamic contour extracting unit 122 uses the initial contour sent from the initial contour extracting unit 121 as the initial value, and applies an active contour model (an active contour model called SNAKES is used for this embodiment) to an object subject to examination within an ultrasound image generated by the image generating unit 110. The dynamic contour extracting unit 122 then regards the applied active contour model as the energy minimization problem in a dynamical system and formulates it, so that the dynamic contour extracting unit 122 finds, as an optimum solution of one type of an optimization problem, a contour pattern that matches best to the contour of the object to be examined.

In more detail, the dynamic contour extracting unit 122 specifies a curve representing the contour while gradually changing and converging a position and a shape of the curve in such a way as to make energy "E" shown in an expression below equal to either a minimum value or a relative minimum value when the curve is represented by an expression, v(s)=(x(s), y(s)). For instance, the contour (curve) may continue to be deformed until fluctuations of the energy "E" for the iterative calculation stabilize within a predetermined range.

Expression: $E=\int\{\text{Eint}(v(s))+\text{Eimage}(v(s))+\text{Econ}(v(s))\}ds$ In the above expression, "Eint" represents a function defining internal energy produced by a bend in the curve, "Eimage" represents a function defining energy that pulls the curve toward edges or the like of an image, and "Econ" represents a function defining energy of an external constraining force.

In order to converge contours by using the SNAKES model, in other words, to minimize the energy value, calculations should be repeated while a certain active construction is applied to a temporally obtained contour. This may be performed by iterative operations, such as the variation method, a method for adding perturbation, and a method called "dynamic programming."

Figure 9A:
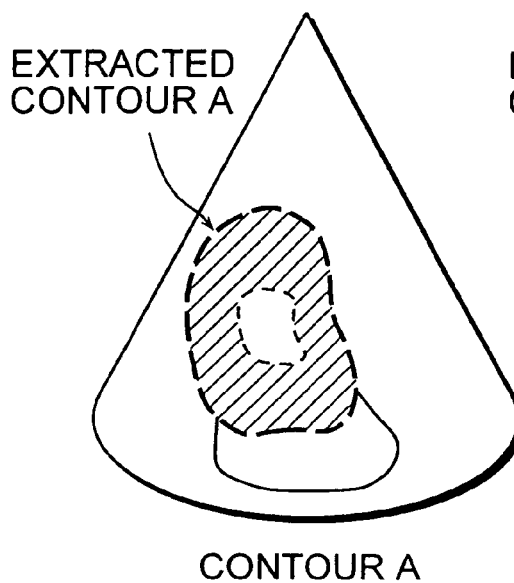
FIGS. 9A–9C show states in which the initial contour extracting unit estimates and generates a new initial contour by using previously extracted contours.
Figure 9B:
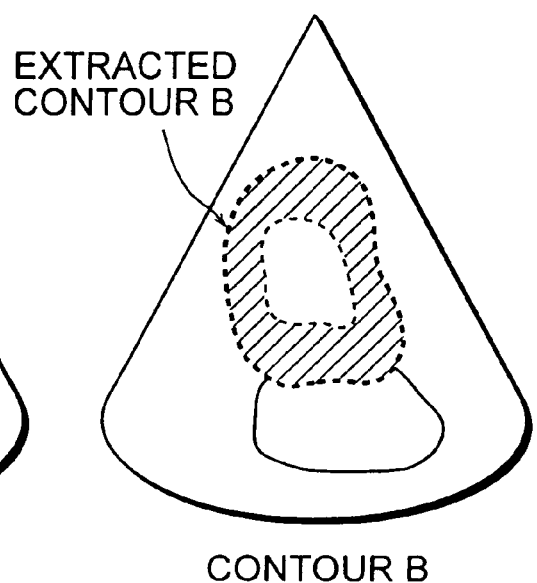
Figure 9C:
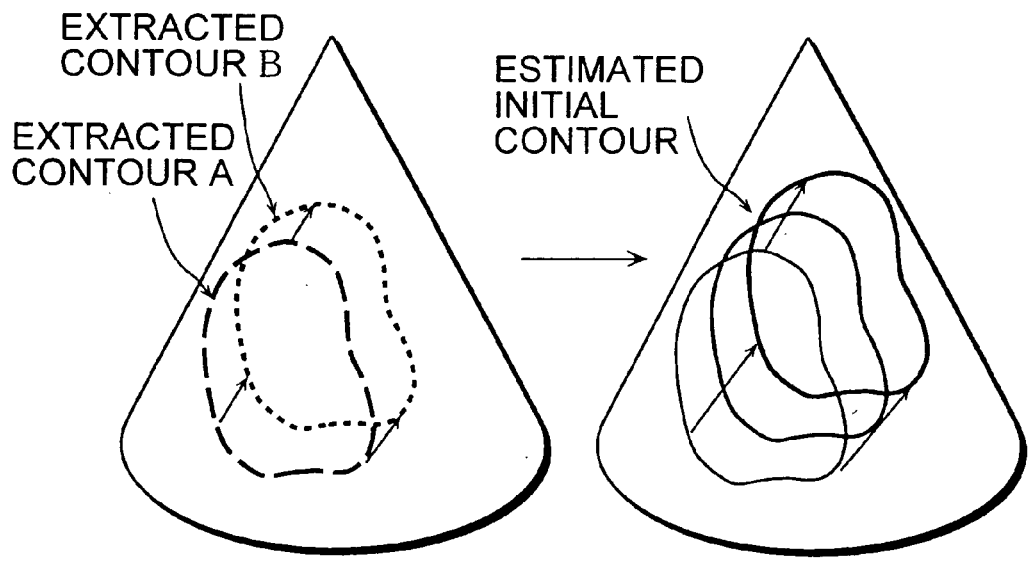

FIGS. 9A–9C are provided to explain how contour data extracted by the dynamic contour extracting unit 122 is used as feedback to the initial contour extracting unit 121. FIGS. 9A–9B show two sets of example contour data (contours "A" and "B") which have been extracted, in its final operational stage, by the automatic contour extracting unit 120 from two ultrasound images successively inputted to the automatic contour extraction unit 120, and FIG. 9C shows a state in which the initial contour extracting unit 121 generates an initial contour for a new ultrasound image from the two extracted contours "A" and "B."

More specifically, the initial contour extracting unit 121 estimates an initial contour of an object of interest within an ultrasound image by predicting movement (i.e., performing movement compensation) of the object from two sets of contour data which have been extracted by the dynamic contour extracting unit 122 immediately before the initial contour to be estimated. For instance, the two sets of contour data precede the initial contour by one frame and two frames, respectively. The initial contour extracting unit 121 then sends the estimated initial contour to the dynamic contour extracting unit 122. The above estimation is performed, for instance, by (1) specifying the same characteristic points (pixels) for the two sets of contour data, (2) calculating a motion vector based on differentials of coordinates of the specified characteristic points, and (3) calculating coordinates of the characteristic points when they are assumed to move at a fixed speed for a fixed period to estimate the initial contour.

As is described above, the automatic contour extracting unit 120 first extracts an initial contour based on a method which is suited to rough extraction, such as the degenerate operation, and then performs a more accurate extraction such as by using the SNAKES model. As compared with a case in which only a dynamic extraction such as that using the SNAKES model is performed, the extraction method of the present embodiment not only offers greatly improved convergence but also reduces overall operational time.

An empirical result obtained for a left ventricle indicates that solely using the SNAKES model as in a conventional technique requires the operator to designate the initial contour and this operator's designation takes several to dozens of seconds. When the designated initial value is not appropriate, a great amount of time is required for a subsequent iterative operation due to the heavy dependency of the SNAKES model on the initial value, and a correct contour cannot be output.

The initial value condition that allows convergence of the SNAKES model to be securely achieved is highly sensitive to an image's states (such as density distribution and noise amount) and to parameters to be set. Accordingly, the designation of the initial value by the operator does not provide a sufficiently reliable index. This is to say, even when the operator sets the initial value for the object of the interest very carefully, a resulting operation may be unexpectedly undesirable. In addition, the operator also needs to set parameters.

If the operator succeeds in setting the appropriate initial value by overcoming the above problems, an operational time taken by a 500-MHz Intel's Pentium 3 CPU to achieve the convergence is about 0.2 to 2.0 seconds. Operational time taken by the initial contour extracting unit 121 is about 0.01 seconds.

Accordingly, with the ultrasonic diagnostic device 10 of the present invention, an operation which conventionally takes several seconds or longer to set the initial contour is no longer necessary. In addition, the operational speed is highly improved.

Moreover, the present ultrasonic diagnostic device 10 can provide initial contours with consistent patterns and conditions since the initial contour extracting unit 121 extracts each initial contour according to a predetermined image processing procedure. As a result, parameters consistent with an initial contour extracted by the initial contour extracting unit 121 can be provided to the dynamic contour extracting unit 122, which is to say, the parameters can be tuned in advance. Consequently, the convergence (or stability) in dynamic contour extraction is greatly enhanced, and the overall operational time is highly reduced.

Accordingly, the operator can benefit from the present invention in that operations that conventionally require the operator's involvement are completely automated, and always-consistent diagnostic information can be obtained.

It is possible to set, in advance, parameters and convergence conditions used in each extraction operation in such a way as to satisfy an expression of $t1 \geq t2$, when "t1" and "t2" represent a duration during which the initial contour extracting unit 121 extracts an initial contour, and a duration during which the automatic contour extracting unit 122 extracts a contour, respectively. With this setting, the initial contour is specified with high accuracy, and the overall time taken by contour extraction can be reduced. On the other hand, it is alternatively possible to set parameters and convergence conditions used for each operation so as to satisfy an expression of $t1 \leq t2$. With this setting, a longer time is taken to dynamically extract a contour so that a highly accurate contour can be obtained.

The following describes the processing of the above ultrasonic diagnostic device 10.

Figure 10:
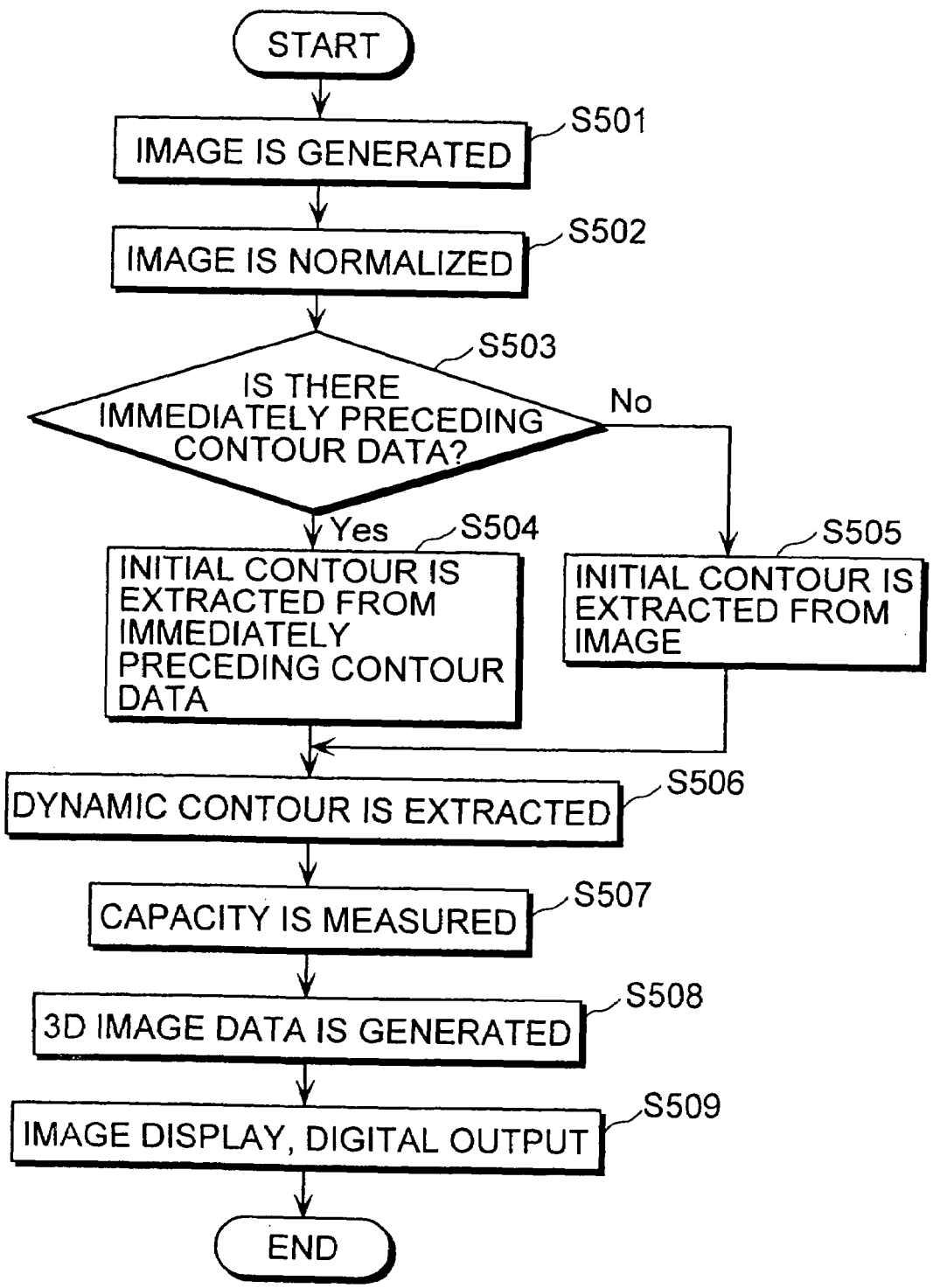
FIG. 10 is a flowchart mainly showing the processing of an image processing unit of the above ultrasonic diagnostic device.

FIG. 10 is a flowchart showing the processing flow of the ultrasonic diagnostic device 10. The shown processing flow is mainly for the image processing unit 103, and corresponds to one cycle to be repeated under the frame-rate control of the real time control unit 113.

The image generating unit 110 performs A/D conversion on a signal from the send/receive unit 102, and has the image normalizing unit 111 normalize a density value of each pixel, so that ultrasonic image data corresponding to one scan by the ultrasonic search unit 101 is generated (steps S501–S502). The generated image data is accumulated by the moving image storing unit 112, and also sent to the automatic contour extracting unit 120.

In the automatic contour extracting unit 120, the initial contour extracting unit 121 judges whether there is contour data extracted from past ultrasound images which the automatic contour extracting unit 120 has received immediately before the currently inputted ultrasound image data (step S503). If so (i.e., the "yes" judgment is made in step S503), the initial contour extracting unit 121 estimates and generates an initial contour of the current ultrasound image from the past contour data (step S504). If no such past contour data exists (i.e., the "no" judgment is made in step S503), the initial contour extracting unit 121 performs, on the current ultrasound image, density correction, binarization, and the degenerate operation to extract a new initial contour (step S505).

Following this, the dynamic contour extracting unit 122 uses the initial contour sent from the initial contour extracting unit 121 as an initial value, and performs iterative calculations using the active contour model to extract an accurate contour (step S506).

The automatic capacity measuring unit 115 applies the approximate expression and the like to the extracted contour to calculate a capacity of the object to be examined (step S507), and the 3D image generating unit 116 accumulates the extracted contour data to produce data for a 3D contour image (step S508).

The ultrasound image display unit 104a presents images, such as the ultrasound image generated by the image processing unit 110 and the object's contour extracted by the automatic contour extracting unit 120, to the display apparatus 11. At the same time, the measurement display unit 104b presents the capacity calculated by the automatic capacity measuring unit 115 to the LCD unit of the probe 13 (step S509).

In this way, the ultrasonic diagnostic device 10 of the present invention displays synchronized images and data, such as a generated ultrasound image, a contour obtained from the generated ultrasound image, and a capacity calculated based on the contour. This allows the operator to examine the object of interest such as a heart from different perspectives in real time.

As to moving images stored in the moving image storing unit 112 and 3D images in the 3D image generating unit 116, the image display unit 104 presents them as either moving images or a still picture to the display apparatus 11 while real-time diagnosis from steps S501 to S509 using a stated frame rate is not performed. In accordance with an instruction given by the operator, the digital output unit 105 outputs digital data concerning the contour and the capacity to a device in the periphery either in parallel with the real-time diagnosis or during a period in which the real-time diagnosis is not performed.

Figure 11:
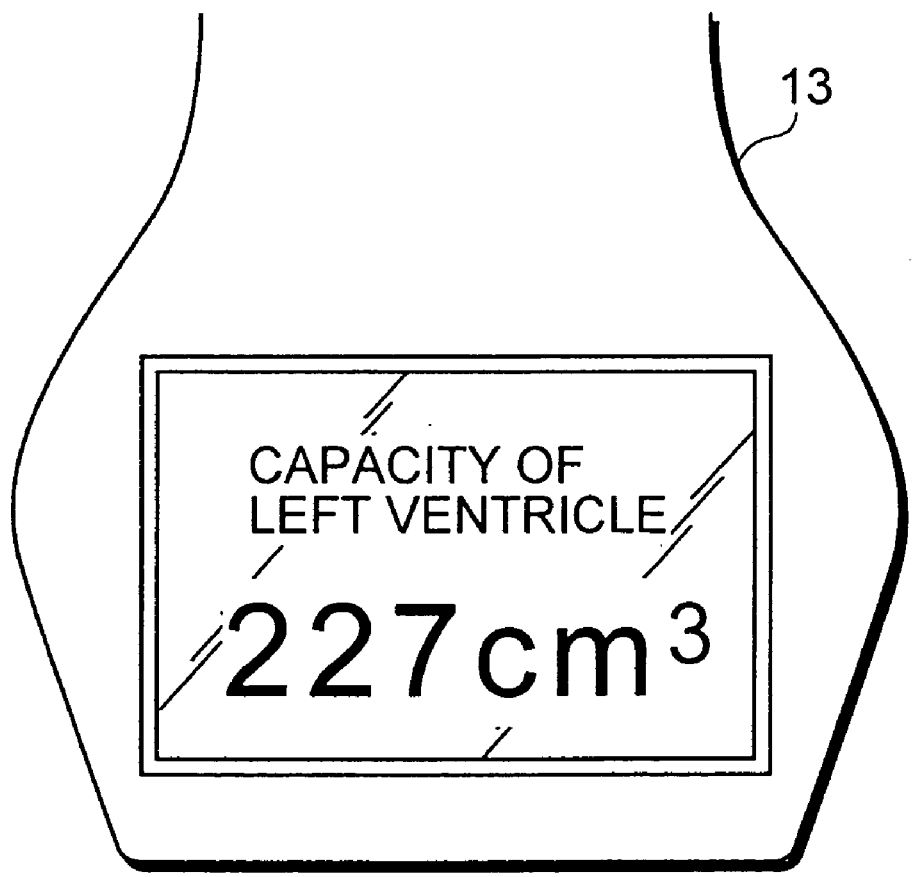
FIG. 11 shows an example of a screen, displaying a capacity of the left ventricle, of a liquid crystal display (LCD) unit in a probe of the ultrasonic diagnostic device.

FIG. 11 shows an example of a screen, which is obtained in the above real-time diagnosis, of the LCD unit in the probe 13. With this example, a capacity of a left ventricle of a heart calculated by the automatic capacity measuring unit 115 is displayed while the capacity is being updated in accordance with the frame rate.

Figure 12:
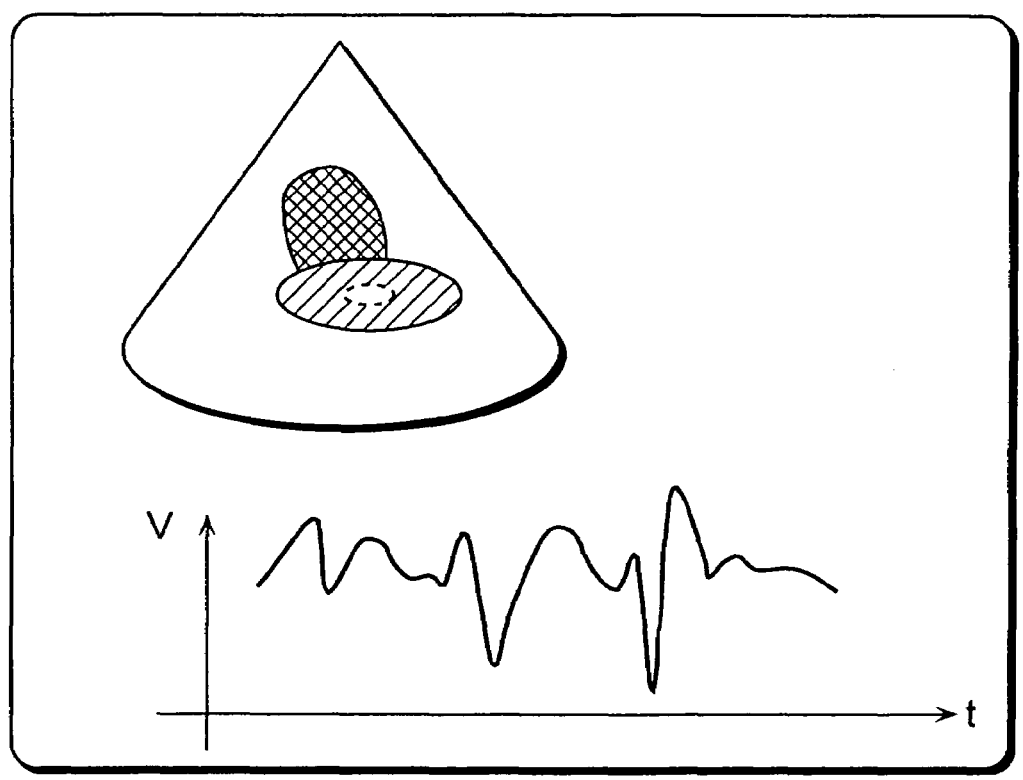
FIG. 12 shows an example of a screen, displaying the contour of the left ventricle and a graph showing change of its capacity over time, of a display apparatus of the ultrasonic diagnostic device.

FIG. 12 shows an example of a screen, which is obtained in the real-time diagnosis, of the display apparatus 11. With this example, an ultrasound image generated for the heart by the image generating unit 110 is displayed in real time. In a lower part of the screen, a graph is superimposed and displayed in a manner that is either asynchronous or synchronous with the display of the ultrasound image. This graph shows a transition of the capacity which is calculated based on the contour of the left ventricle over time.

As has been described, the ultrasonic diagnostic device 10 of the present embodiment allows the automatic contour extracting unit 120 to automatically extract a contour of an object subject to examination from an ultrasound image. Accordingly, the operator can obtain the accurate contour and a capacity of the object in real time by only moving the probe 13 in a part of a patient's body without needing to perform any operations such as the designation of an initial contour during diagnosis.

Second Embodiment

The following describes an ultrasonic diagnostic device 20 according to the second embodiment of the present invention. This ultrasonic diagnostic device 20 is the same as the diagnostic device 10 of the first embodiment in that the ultrasonic diagnostic device 20 automatically extracts a contour of an object from continuously generated ultrasound images and calculates a capacity of the object by using the extracted contour. The two ultrasonic diagnostic devices 10 and 20 differ, however, in that the ultrasonic diagnostic device 20 of the second embodiment uses a plurality of ultrasound images corresponding to different cross sections of the same object to calculate a capacity with high accuracy. The ultrasonic diagnostic device 20 also differs from the ultrasonic diagnostic device 10 in that the ultrasonic diagnostic device 20 displays synchronized images of different cross sections.

Figure 13:
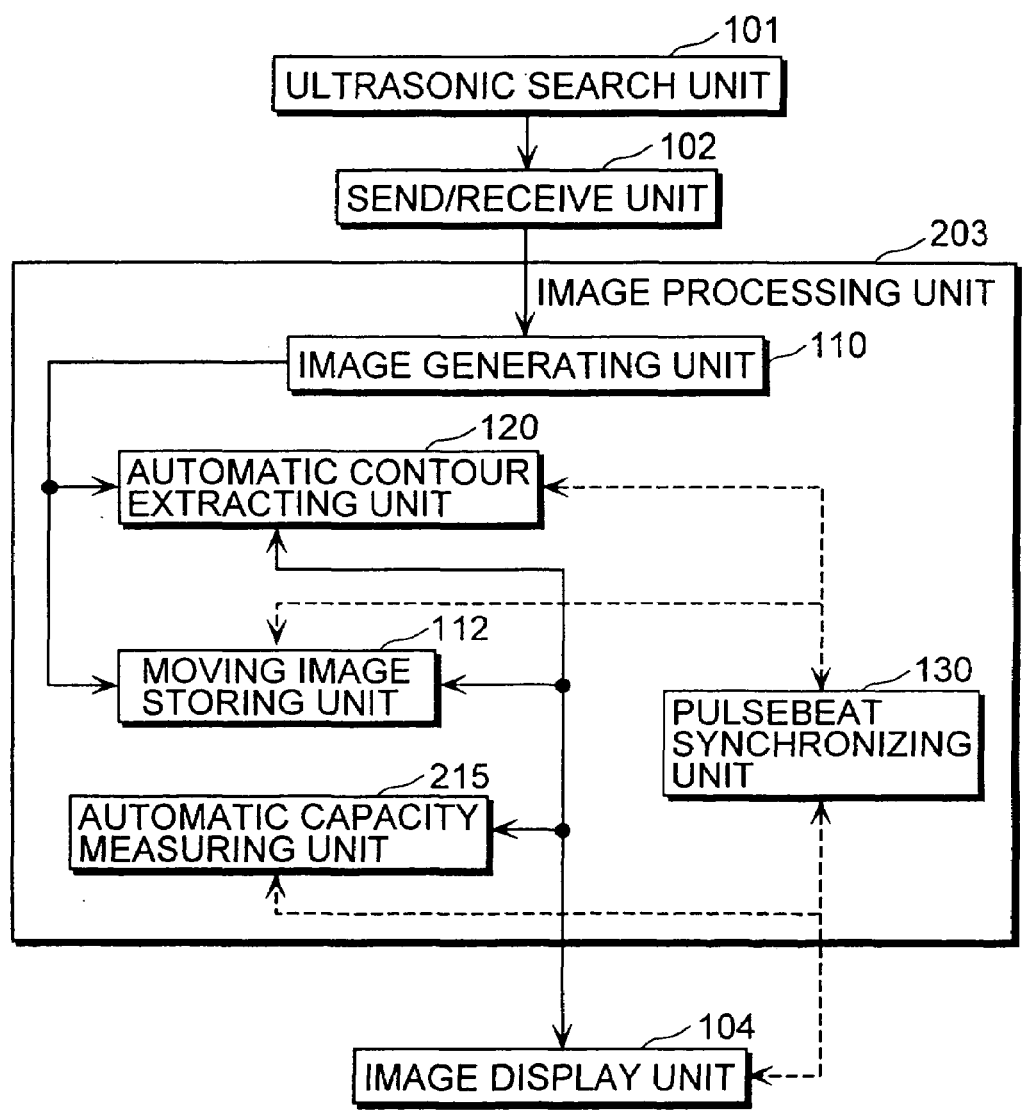
FIG. 13 is a block diagram showing a function configuration of an ultrasonic diagnostic device of the second embodiment according to the present invention.

FIG. 13 is a block diagram showing a function configuration of the ultrasonic diagnostic device 20 of the second embodiment. In FIG. 13, units that are the same as those in the first embodiment are either omitted or given the same reference numbers as used in the first embodiment, and will not be described, with this being the case for the subsequent figures.

An image processing unit 203 of the present ultrasonic diagnostic device 20 includes an automatic contour extracting unit 120, a moving image storing unit 112, a pulsebeat synchronizing unit 130, and an automatic capacity measuring unit 215. This image processing unit 203 differs from the first embodiment in that the image processing unit 203 includes the pulsebeat synchronizing unit 130 and the automatic capacity measuring unit 215 that calculates a capacity with higher accuracy than the first embodiment.

The pulsebeat synchronizing unit 130 associates an ultrasound image with another ultrasound image, which are obtained in different periods and correspond to different cross sections. The pulsebeat synchronizing unit 130 then controls units 120, 112, 215, and 104 in such a way as to synchronize the associated ultrasound images in accordance with a pulsebeat that is indicated by a blood-flow waveform sent from an electrocardiogram (ECG) measuring instrument (not shown in FIG. 13). In other words, the pulsebeat synchronizing unit 130 performs control operation to process the associated ultrasound images as a group of images of the same object under the same state.

In more detail, while interacting with the operator, the pulsebeat synchronizing unit 130 controls the automatic contour extracting unit 120 and the moving image storing unit 112 so as to make the moving image storing unit 112 accumulate ultrasound images corresponding to different cross sections of the same object, and to make the automatic contour extracting unit 120 extract a contour from each of these ultrasound images. For instance, the moving image storing unit 112 is controlled to accumulate two-chamber and four-chamber ultrasound images of a left ventricle of a heart which are obtained by turning the probe 13 at 90 degrees (or any given degrees, such as 120 and 30 degrees) over a period corresponding to at least one pulsebeat cycle. The automatic contour extracting unit 120 is controlled to extract a contour of an inner wall of the left ventricle from each of the above two types of ultrasound images.

The pulsebeat synchronizing unit 130 then specifies a pair of ultrasound images (hereafter referred to as an image pair) and a pair of contour data (hereafter referred to as a contour pair) from the above two types of a sequence of ultrasound images and that of contour data, respectively. Images in each specified image pair correspond to the same phase (i.e., relatively the same time in a pulsebeat cycle), and so does contour data in each specified contour pair. The pulsebeat synchronizing unit 130 then has the moving image storing unit 112 send the specified image pair to the image display unit 104, and has the automatic contour extracting unit 120 send the specified contour pair to the automatic capacity measuring unit 215. The pulsebeat synchronizing unit 130 repeats the above series of operations for each phase.

As shown in FIG. 14, the automatic capacity measuring unit 215 specifies cross-sectional areas "A1" and "A2", and major axes "h1" and "h2" of the contour pair sent from the automatic contour extracting unit 120 to calculate a capacity of the object by using an approximate expression in accordance with the biplane area length method. This approximate expression uses two cross sections that are orthogonal to each other, and yields a more accurate capacity than the single-plane-area approximate expression used in the first embodiment.

Figure 15:
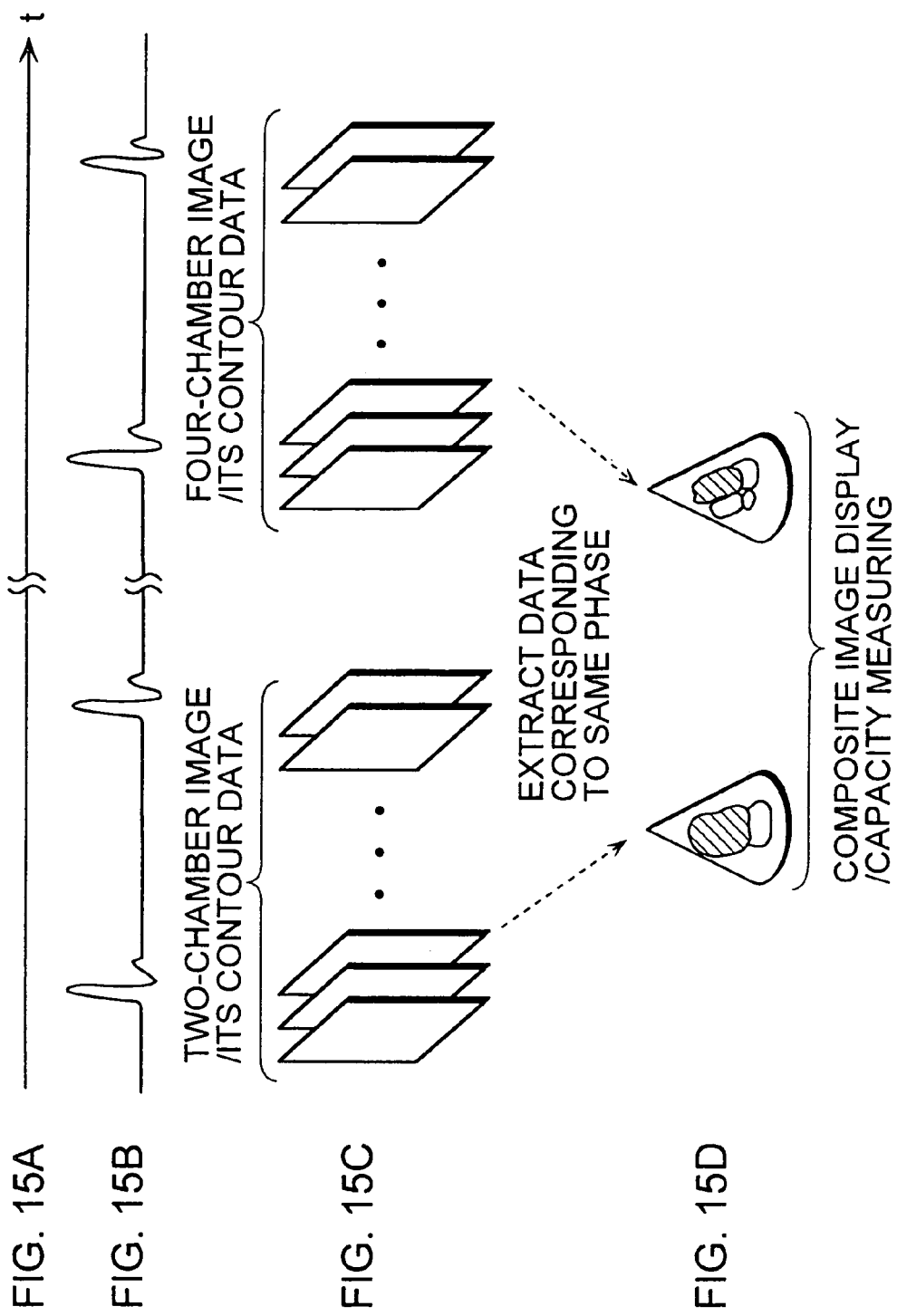
FIGS. 15A–15D are diagrams used to explain the control processing of a pulsebeat synchronizing unit of the ultrasonic diagnostic device.

FIGS. 15A–15D are used to explain control operations of the pulsebeat synchronizing unit 130. FIGS. 15A and 15B show a time axis and pulsebeats (a blood-flow waveform), respectively. FIG. 15C shows an example of sequences of ultrasound images (or contour data extracted from these ultrasound images), which are obtained over different periods for cross sections that are orthogonal to each other. For this example, the sequences of ultrasound images are for two-chamber and four-chamber views of the heart. FIG. 15D shows a state in which an image pair and a contour pair are used for image display and capacity calculation, respectively. The image pair and the contour pair are selected from the above two types of ultrasound image sequences and contour data sequences, and consist of images and contour data, respectively, with the same phase.

Figure 16:
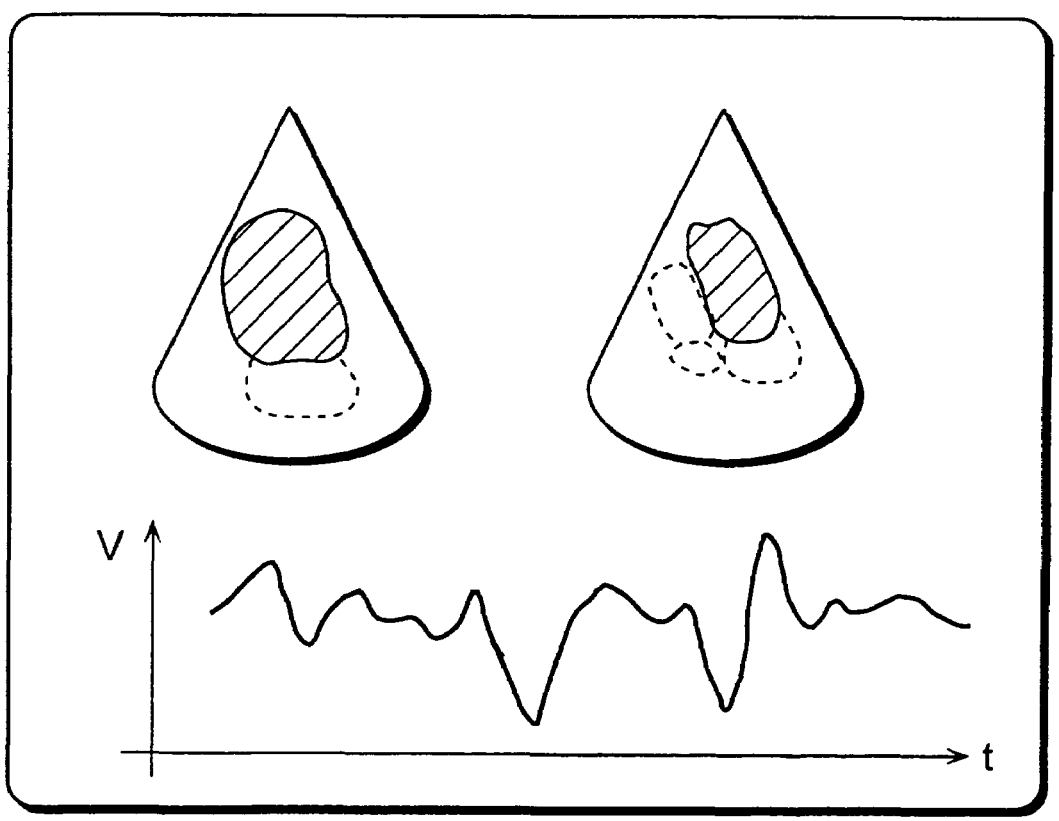
FIG. 16 shows an example of a screen, displaying contours of organs such as a left ventricle of a heart and a graph showing changes in its capacity over time, of a display apparatus of the ultrasonic diagnostic device.

FIG. 16 shows an example of a screen of the object's contours and capacity obtained under the control of the pulsebeat synchronizing unit 130. For this example, the image display unit 104 presents a graph showing the transition of the capacity of the left ventricle over time in a lower part of the screen of the display apparatus 11. In synchronization with this presentation, the image display unit 104 also presents a contour of the left ventricle in a two chamber view at the upper left portion of the screen, and a contour of the left ventricle in a four chamber view at the upper right portion of the screen.

As has been described, the present ultrasonic diagnostic device 20 has the pulsebeat synchronizing unit 130 specify an image pair and a contour pair that consist of ultrasound images and sets of contour data, respectively, with the same phase out of a plurality of ultrasound image sequences and contour data sequences obtained over different periods. As the present ultrasonic diagnostic device 20 performs image processing while treating images and contour data within each specified pair as a group of information concerning the same state of the same object, the ultrasonic diagnostic device 20 can provide highly detailed and accurate diagnostic results.

Example Modifications

The following describes example modifications of the ultrasonic diagnostic devices 10 and 20 and their elements of the first and second embodiments.

An example modification relating to an image normalizing unit 211 that can replace the image normalizing unit 111 described in the above embodiments is described first.

Figure 17A:
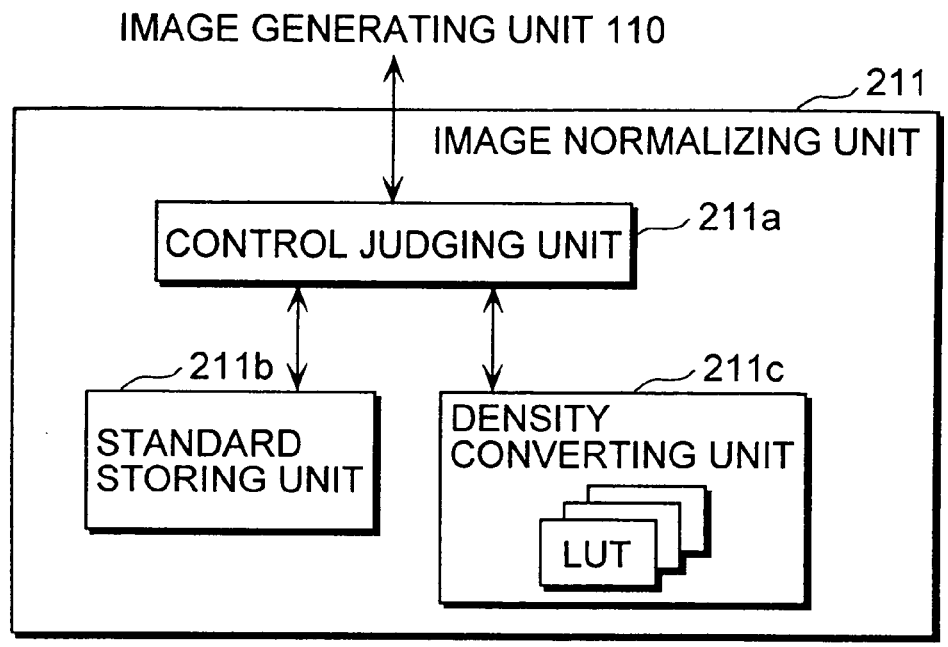
FIG. 17A is a block diagram showing a function configuration of an image normalizing unit according to an example modification.
Figure 17B:
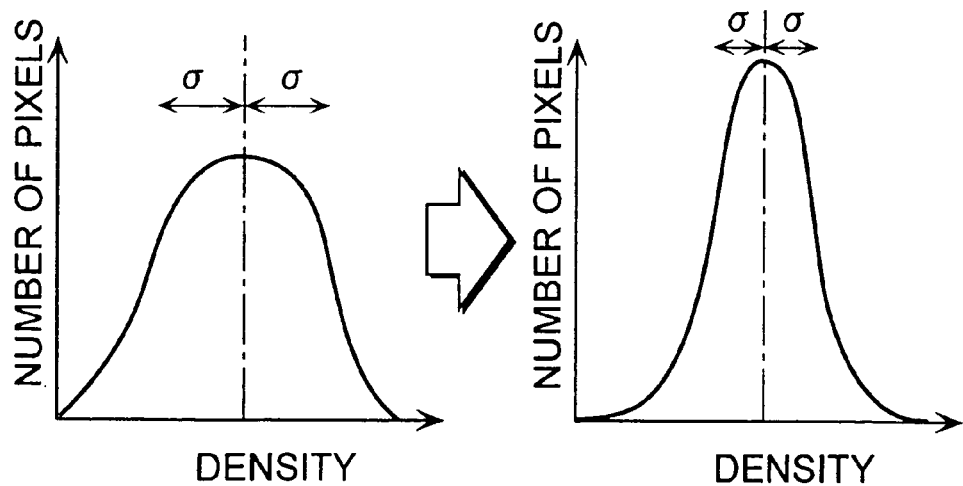
FIG. 17B is a density distribution transition diagram, which shows contents of normalization performed by the normalizing unit on an ultrasound image.

FIG. 17A is a block diagram showing a detailed construction of the image normalizing unit 211. FIG. 17B illustrates contents of normalization performed by the normalizing unit 211 for an ultrasound image. FIG. 17B shows a transition of density distribution of the ultrasound image.

This image normalizing unit 211 is unique in that it performs different normalization for each object to be examined, and the image normalization unit 211 selects a conversion operation that is best suited for the object and performs the selected conversion operation to normalize an ultrasound image of the object. The image normalizing unit 211 includes a control judging unit 211a, a standard storing unit 211b, and a density converting unit 211c.

The standard storing unit 211b is a rewritable memory storing in advance normalization standards (i.e., indexes showing how density distribution should be converted) which are associated with each type of an object subject to examination. The operator can edit and set contents of the standard storing unit 211b in advance.

The stored normalization standards may be, for instance, standard parameters for normalization that produces an image of a heart in which a left ventricle is presented more clearly than other parts of the heart, and an image of a fetus whose surface parts are clearly presented. More specifically, one of the stored normalization standards may be, with a premise that density distribution of an ultrasound image is Gaussian distribution, for making an average density value in a predetermined region around the center of the ultrasound image half a dynamic range value, and another standard may be for making a variance of the density distribution in the predetermined region one-tenth the dynamic range (as in conversion shown in FIG. 17B).

The density converting unit 211c stores in advance LUTs corresponding to a plurality of transform functions. Upon receiving an ultrasound image and a designated region in the image, the density converting unit 211c converts the density of each pixel of the designated region by using each of the plurality of LUTs to generate a plurality of sets of image data, and sends them back to the control judging unit 211a.

By communicating with the standard storing unit 211b and the density converting unit 211c, the control judging unit 211a controls operations to perform normalization that best matches the normalization standard determined by a type or other property of the object.

Figure 18:
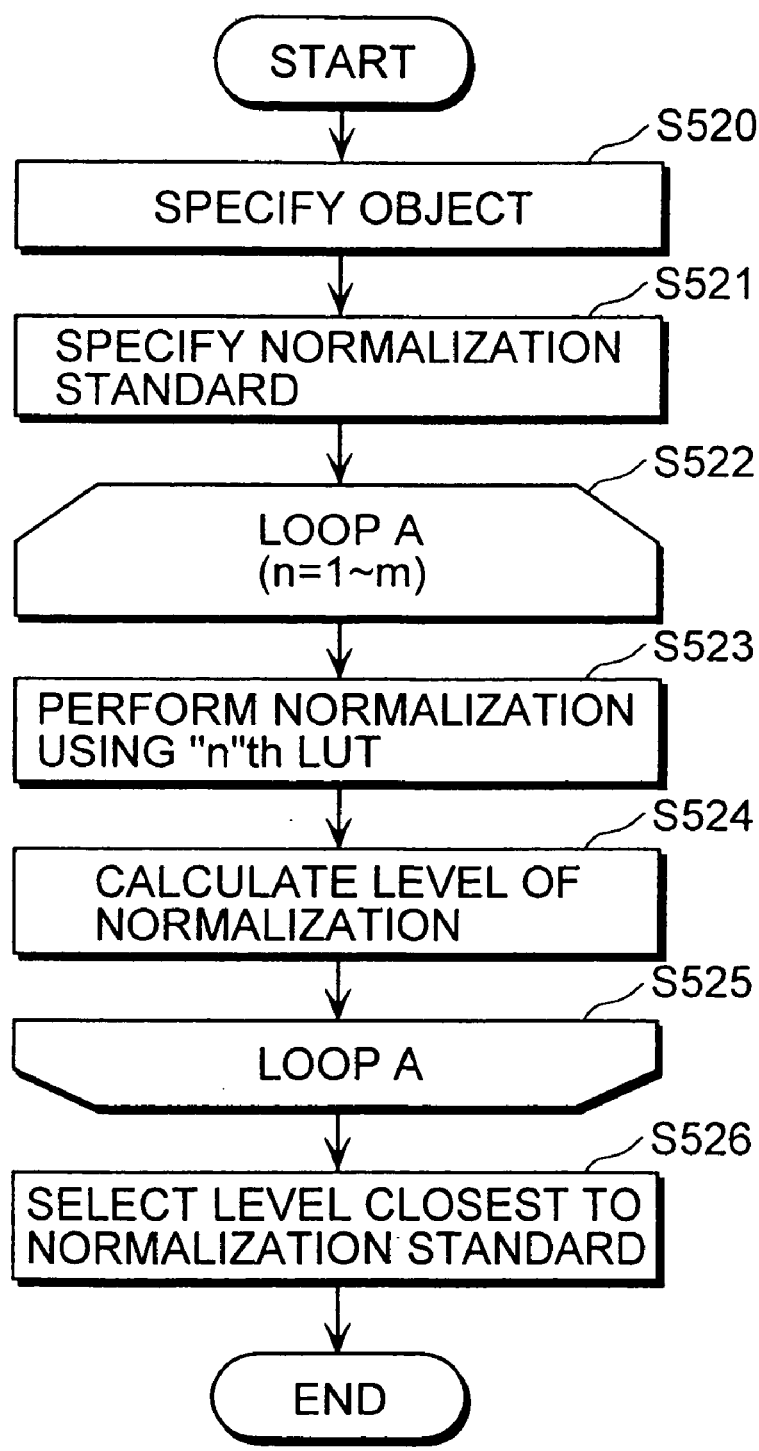
FIG. 18 is a flowchart showing the processing of the image normalizing unit.

FIG. 18 is a flowchart showing the processing of the image normalizing unit 211. Upon receiving an ultrasound image from the image generating unit 110, the control judging unit 211a specifies an object to be examined and a region to be normalized in accordance with either an instruction given by the operator beforehand, or contours of objects extracted in the past (step S520). The control judging unit 211a then reads from the standard storing unit 211b a normalization standard which is associated with the specified object (step S521).

After this, the control judging unit 211a sends the ultrasonic image containing the specified region to be normalized to the density converting unit 211c, and has the density converting unit 211c convert the sent ultrasound image to generate a set of image data (step S523). The control judging unit 211a then evaluates a level of normalization performed on the generated set of image data (step S524). The control judging unit 211a repeats these operations from steps S523–S524 a number of times equal to a number of LUTs stored in the density converting unit 211c (steps S522–S525). For instance, if the read normalization standard relates to variance, the control judging unit 211a evaluates a level of the conducted normalization by calculating a variance of density distribution of each set of the generated image data in step S524.

Out of the plurality of evaluated levels, the control judging unit 211a specifies one level that is closest to the read normalization standard, and then sends the generated set of image data corresponding to the specified level to the image generating unit 110 as a normalized ultrasound image (step S526). For example, the control judging unit 211a specifies, out of calculated variance values, a variance value closest to one-tenth of the dynamic range, and returns a set of image data corresponding to the specified variance to the image generating unit 110.

This image normalizing unit 211 performs flexible normalization, instead of fixed normalization, by selecting a normalization that is best suited to an object to be examined. This allows subsequent image processing, such as contour extraction, to be accurately performed at a higher speed.

The following describes another example modification relating to an automatic contour extracting unit 220 that can replace the automatic contour extracting unit 120 of the above embodiments.

Figure 19:
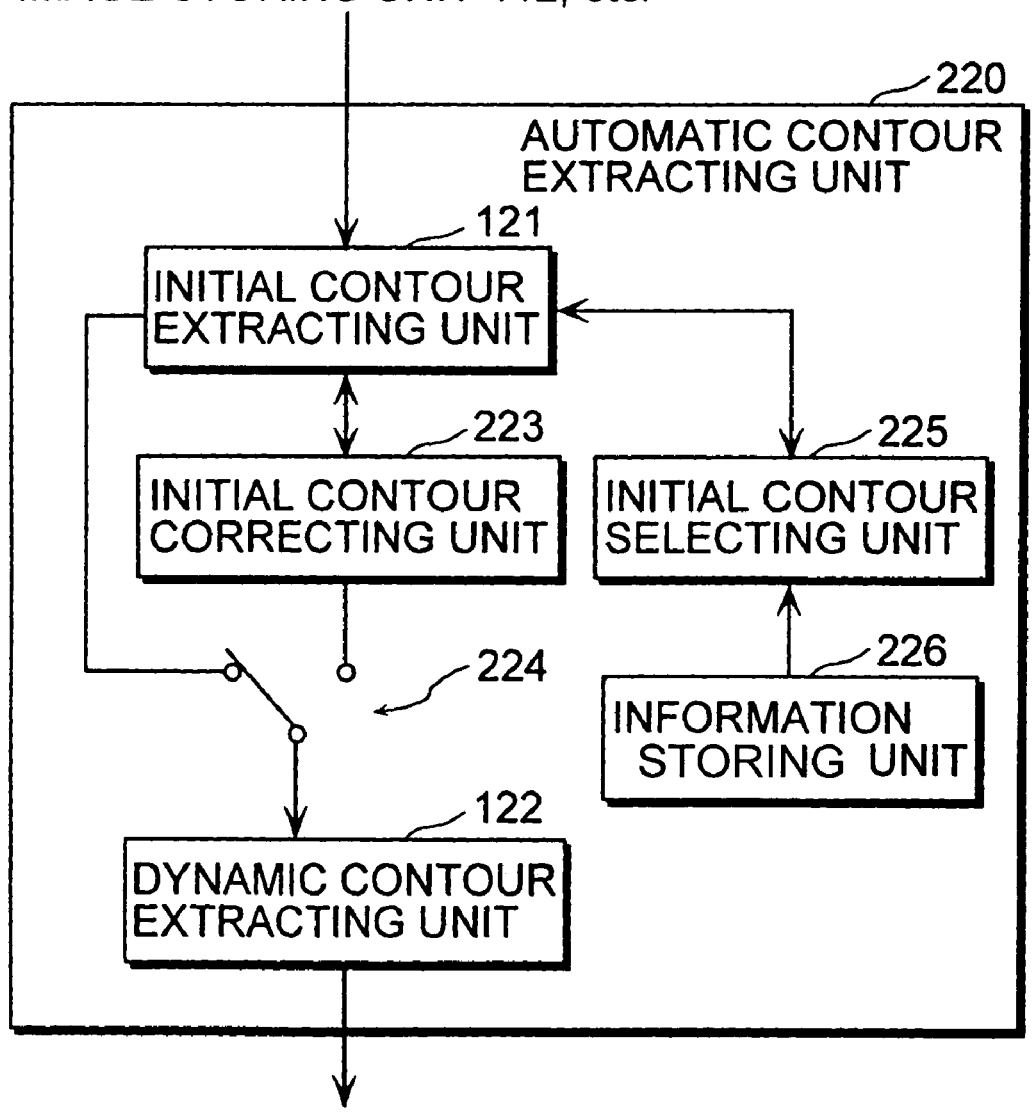
FIG. 19 is a block diagram showing a function configuration of an automatic contour extracting unit according to an example modification.

FIG. 19 is a block diagram showing a construction of the automatic contour extracting unit 220 of the present example modification. In addition to the elements of the automatic contour extracting unit 120 of the above embodiments, the present automatic contour extracting unit 220 includes an initial contour correcting unit 223, an input selecting unit 224, an initial contour selecting unit 225, and an information storing unit 226.

The initial contour correcting unit 223 corrects a shape and a position of an initial contour extracted by the initial contour extracting unit 121 so as to stabilize subsequent extraction by the dynamic contour extracting unit 122. The initial contour correcting unit 223 returns the corrected initial contour to the initial contour extracting unit 121, or outputs the corrected initial contour to the dynamic contour extracting unit 122 via the input selecting unit 224.

In more detail, the initial contour correcting unit 223 calculates a deviation in a position of the initial contour extracted by the initial contour extracting unit 121 by comparing a center position and a moment quantity of the initial contour with those obtained from information regarding regions within the ultrasound image around this initial contour. Upon detecting that the calculated deviation value is higher than a predetermined value, the initial contour correcting unit 223 moves the center of the initial contour to a position between the above positions of centers. The initial contour correcting unit 223 may also change a parameter (such as a threshold value for the stated binarization) that is used for the extraction of the initial contour, and has the initial contour extracting unit 121 extract the initial contour again.

In accordance with an instruction and the like given by the operator in advance, the input selecting unit 224 selects one of the following two control flows: (i) returning the result of correction by the initial contour correcting unit 223 to the initial contour extracting unit 121 to allow the initial contour extracting unit 121 to extract the initial contour again, and having the dynamic contour extracting unit 122 extract a contour; and (ii) giving the correction result of the initial contour correcting unit 223 directly (by feed-forward operation) to the dynamic contour extracting unit 122, and having the contour extracting unit 122 extract a contour. This selection allows an initial contour extraction to be repeated a given number of times in accordance with necessity.

By referring to criterion information stored in the information storing unit 226, the initial contour selecting unit 225 selects either one or at least two designated contours out of a plurality of contours extracted by the initial contour extracting unit 121. The initial contour selecting unit 225 then sends the selected contours to the initial contour extracting unit 121, which sends the contours as initial contours to the initial contour correcting unit 223 and the dynamic contour extracting unit 122.

Note that the initial contour selecting unit 225 is allowed to select a plurality of contours because a single ultrasound image often contains a plurality of regions and objects of interest. In such a case, the contour selecting unit 225 enables the selected plurality of objects to be processed and analyzed in parallel in subsequent operations.

The information storing unit 226 stores beforehand the criterion information, such as that relating to positions, shapes, sizes, and a position relative to other initial contours, which specify organs and cavities that are important for diagnosis. The stored criterion information may indicate for a heart that its left ventricle is often an object that is subject to examination, takes a bell-like shape in an upper center of the ultrasound image, is larger than other cavities (such as a left atrium, a right atrium, and a right ventricle), and lies in a region at the upper right.

By referring to such criterion information as described above, the initial contour selecting unit 225 is capable of accurately selecting a contour (of the left ventricle) specified by the criterion information.

With the provision of the above units, such as the initial contour correcting unit 223 and the initial contour selecting unit 225, an initial contour extracted by the initial contour extracting unit 121 is sent to the dynamic contour extracting unit 122 not directly but through correction and selection made from a variety of viewpoints. This can improve convergence in the iterative calculation by the dynamic contour extracting unit 122.

The following describes another example modification incorporating an image processing unit 303 that can replace the image processing unit 103 described in the above embodiments.

Figure 20:
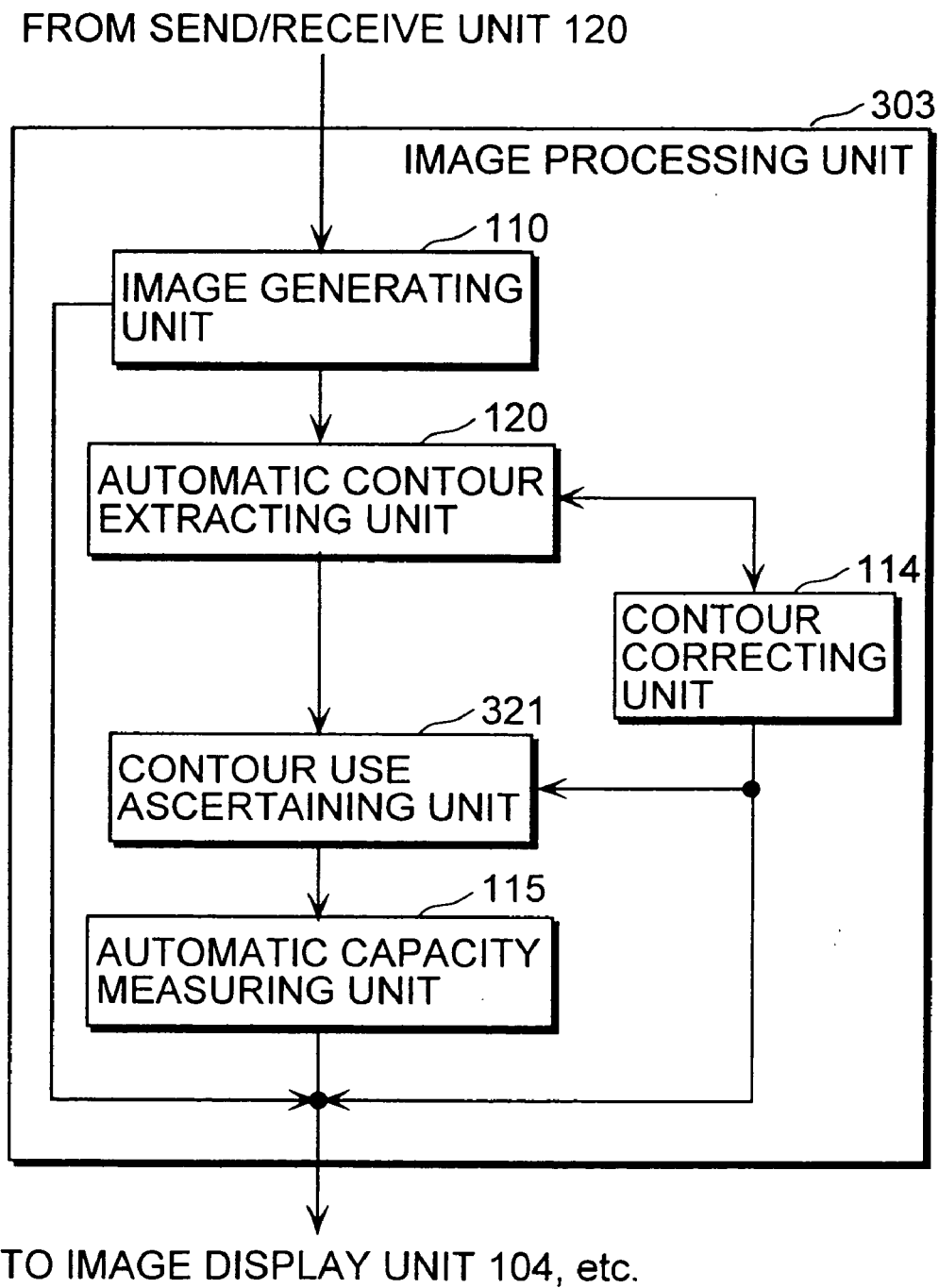
FIG. 20 is a block diagram showing a function configuration of an image processing unit according to an example modification.

FIG. 20 is a block diagram showing a construction of the image processing unit 303 of the present modification. The image processing unit 303 includes, in addition to the units included in the stated image processing unit 103, a contour use ascertaining unit 321 which allows the operator to select whether an automatically extracted contour should be used for the subsequence operations.

The contour use ascertaining unit 321 uses a graphical user interface (GUI) to communicate with the operator by presenting contours either extracted by the automatic contour extracting unit 120 or corrected by the contour correcting unit 114 to the display apparatus 11. The use ascertaining unit 321 then receives an operator's instruction regarding the use of the presented contours to allow the subsequent operations to be performed based on the operator's instruction.

Figure 21:
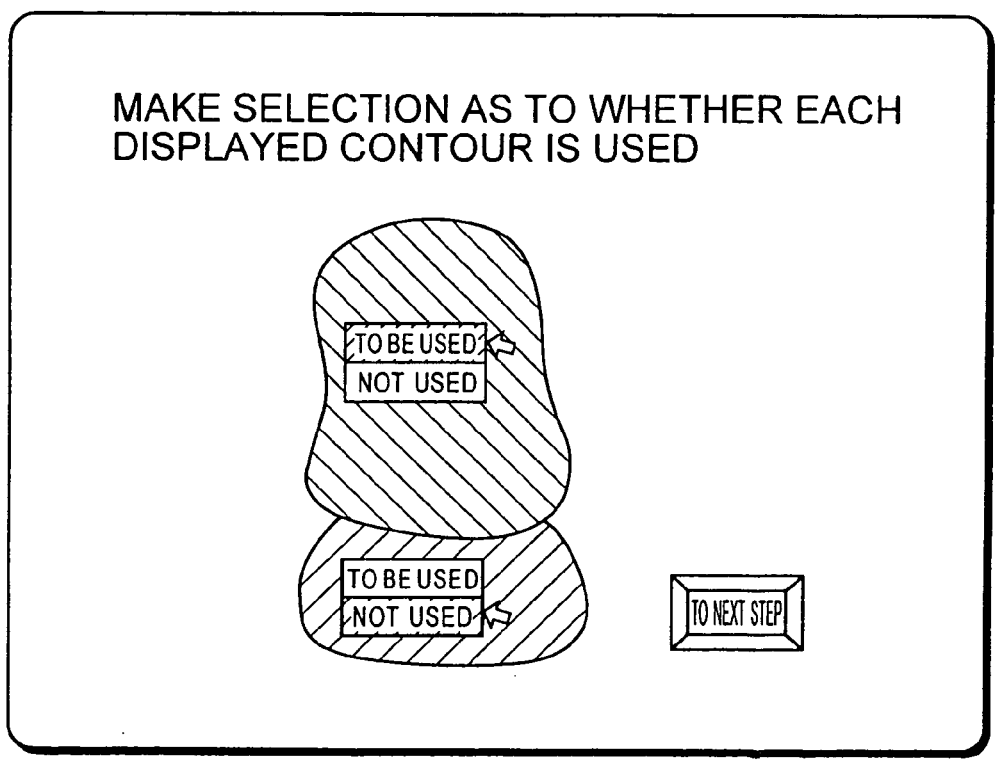
FIG. 21 shows an example of a dialog screen provided by a contour use ascertaining unit of the image processing unit to interact with the operator.

More specifically, the contour use ascertaining unit 321 receives an operator's instructions indicating, for every contour displayed by the display apparatus 11, whether the contour is used for the subsequent operations via a track ball, a mouse, a stylus, and the like, as shown in FIG. 21. The use ascertaining unit 321 then only sends data on contours indicated by the operator's instruction that it should be processed by subsequent units (such as a contour correcting unit 114, an automatic capacity measuring unit 115, a 3D image generating unit 116, and an image display unit 104). In this way, contours are selected for subsequent operations.

This not only achieves correct diagnosis for which extraction result of the automatic contour extracting unit 120 reflects an operator's purpose, experience, and knowledge concerning diagnosis, but also limits objects to be examined to a certain object and prevents incorrect diagnosis from being conducted due to a virtual image resulting from the refraction of ultrasound in the living body.

The following describes example modifications regarding methods for using past extraction results for initial contour extraction.

With the above embodiments, the initial contour extracting unit 121 generates a new initial contour by predicting the movement of the object of interest from a plurality of contours extracted immediately before this new initial contour when frames are continuously inputted at a certain frame rate, as shown in FIGS. 9A–9C. This method may be replaced by other methods described below.

Figure 22:
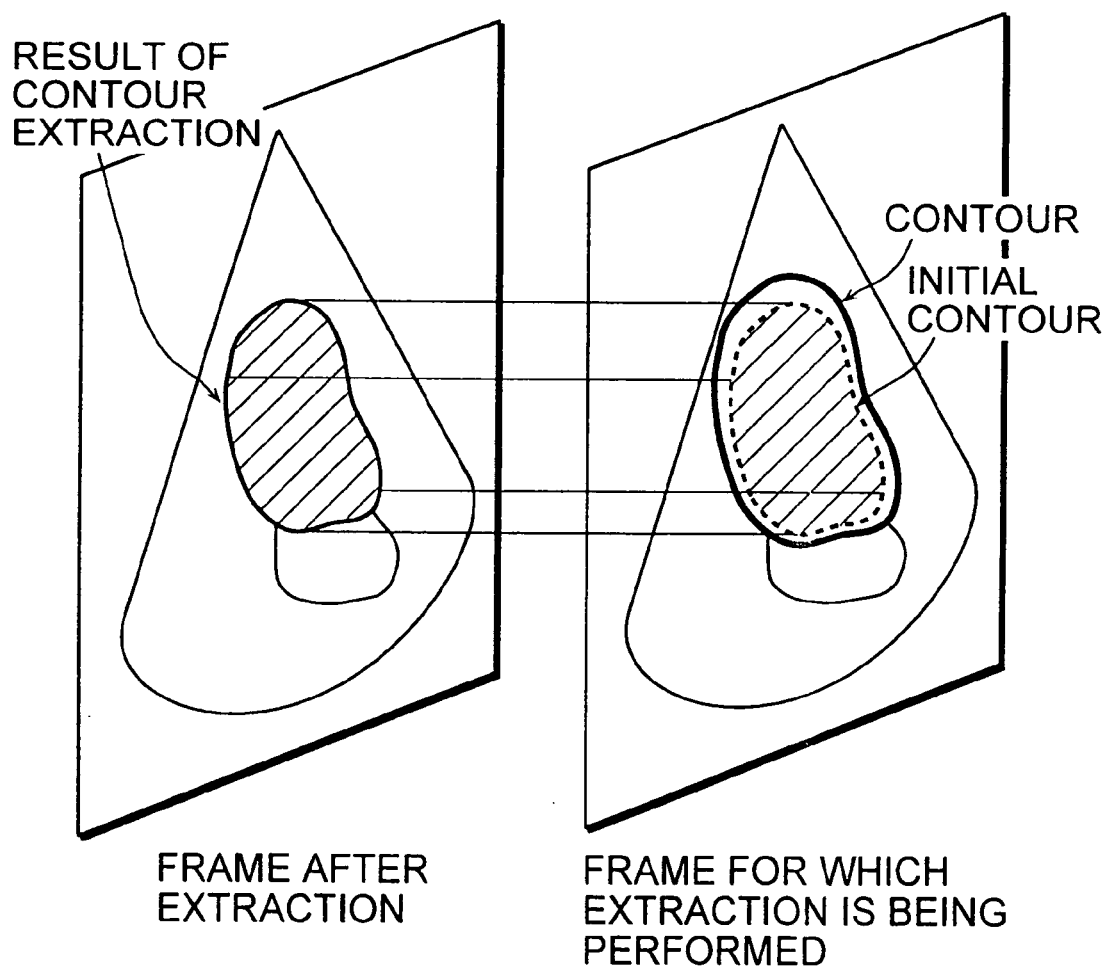
FIG. 22 shows an example modification to a method used by the initial contour extracting unit to generate a new initial contour by using a previously extracted contour, with this example showing the previously extracted initial contour being used as a new initial contour.

For instance, the initial contour extracting unit 121 may use a contour, which has been most recently extracted by the dynamic contour extracting unit 122, as an initial contour that follows this extracted contour, as shown in FIG. 22. Such a simple (high-speed) operation is sufficient when a frame rate is high or movement of the object is small.

When the real-time contour extraction is not necessary (i.e., when contour extraction does not have to be performed for ultrasound images in order of their generation), it is alternatively possible to generate (estimate) an initial contour within an ultrasound image through interpolation using past results of extraction from a plurality of ultrasound images (of frames) which have been obtained immediately before and after the ultrasound image containing the initial contour to be estimated.

Figure 23A:
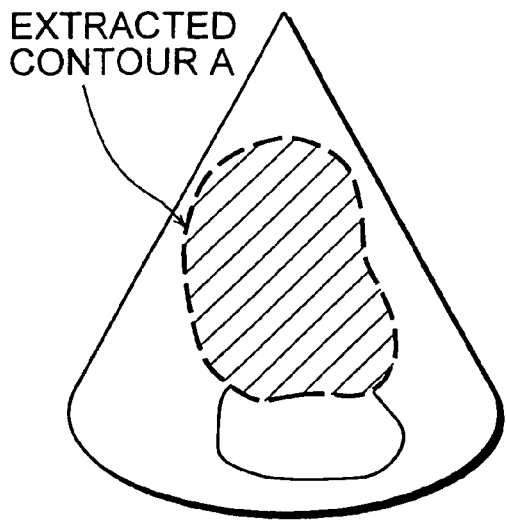
FIGS. 23A–23C show an example modification to a method used by the initial contour extracting unit to generate a new initial contour by using a previously extracted contour, with this example showing a new initial contour being generated through interpolation.
Figure 23B:
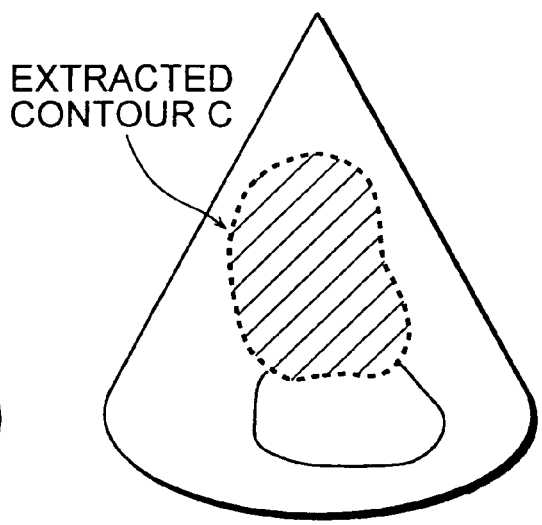
Figure 23C:
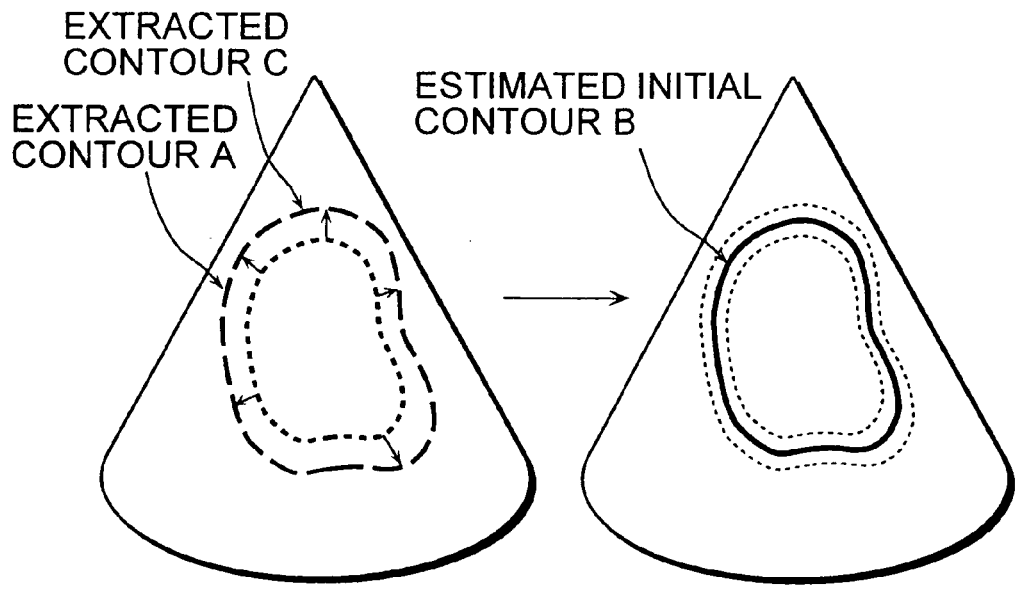

FIGS. 23A–23C show a method for generating an initial contour through such interpolation. In FIGS. 23A–23C, contours are expressed from the oldest to newest as contours "A", "B", and "C." With this method, the initial contour "B" is generated (estimated) from two already extracted contours "A" and "C", which respectively correspond to times before and after a time corresponding to the ultrasound image containing the estimated contour "B."

Figure 24A:
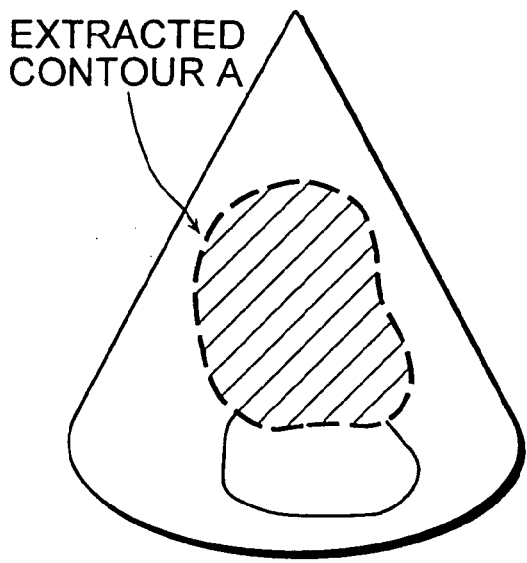
FIGS. 24A–24C show an example modification to a method used by the initial contour extracting unit to generate a new initial contour by using a previously extracted contour, with this example showing a new initial contour being generated through an OR operation.
Figure 24B:
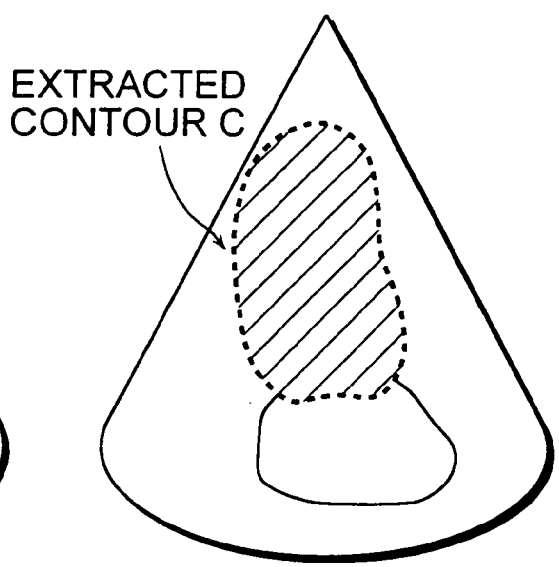
Figure 24C:
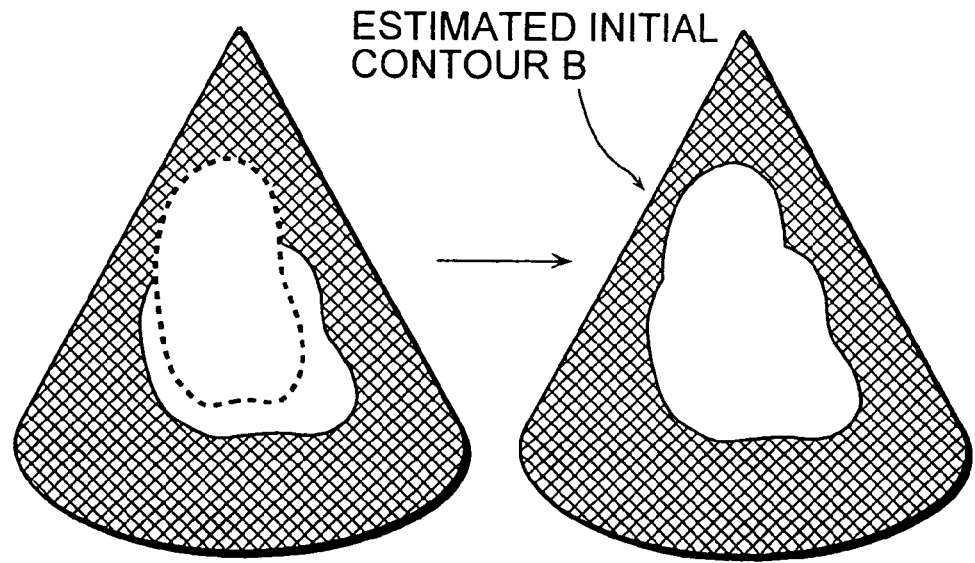
Figure 25A:
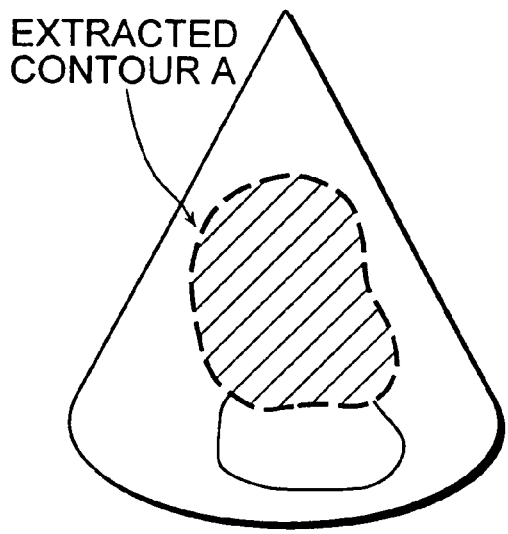
FIGS. 25A–25C show a modification method (which is used by the initial contour extracting unit to generate a new initial contour by using a previously extracted contour, with this example showing a new initial contour being generated through an AND operation.
Figure 25B:
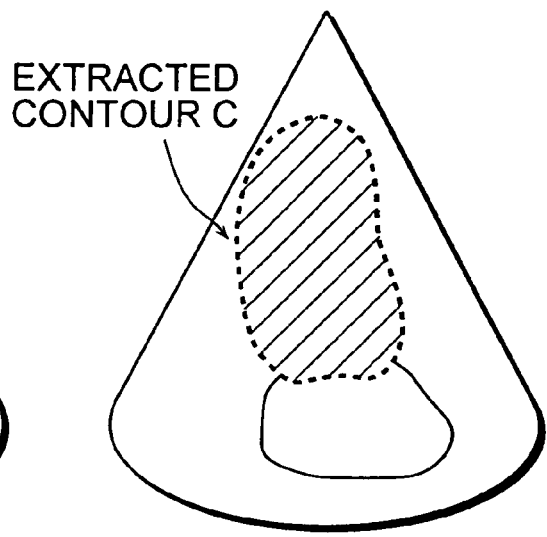
Figure 25C:
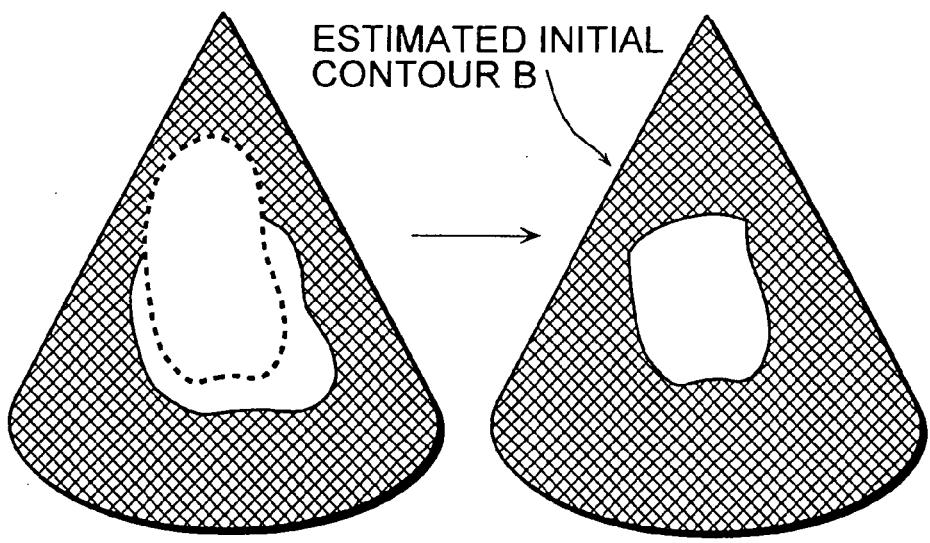

Specifically, this estimation (calculation) may be performed, for instance, by calculating an average of the same characteristic points of the extracted contours "A" and "C" to regard the calculated average as a coordinate of the estimated initial contour "B." It is alternatively possible to regard, as an estimated initial contour "B", a contour that surrounds a region (for which the stated binarization has been performed) generated by the OR operation using two regions surrounded by the extracted contours "A" and "C", as shown in FIGS. 24A–24C. Instead of the above OR operation, the AND operation may be performed, as shown in FIGS. 25A–25C.

From the above methods for estimating an initial contour, a desirable method may be selected in accordance with an object's type, changing state and speed of the object's shape, and the like.

The following describes an example modification relating to methods for calculating the capacity of an object of interest by using an extracted contour of the object.

The automatic capacity measuring units 115 and 215 of the first and second embodiments calculate the capacity of the object by using approximate expressions in accordance with the single plane area length method and the biplane area length method, respectively. Instead of such approximate expressions, other expressions may be used for the present invention.

Figure 26:
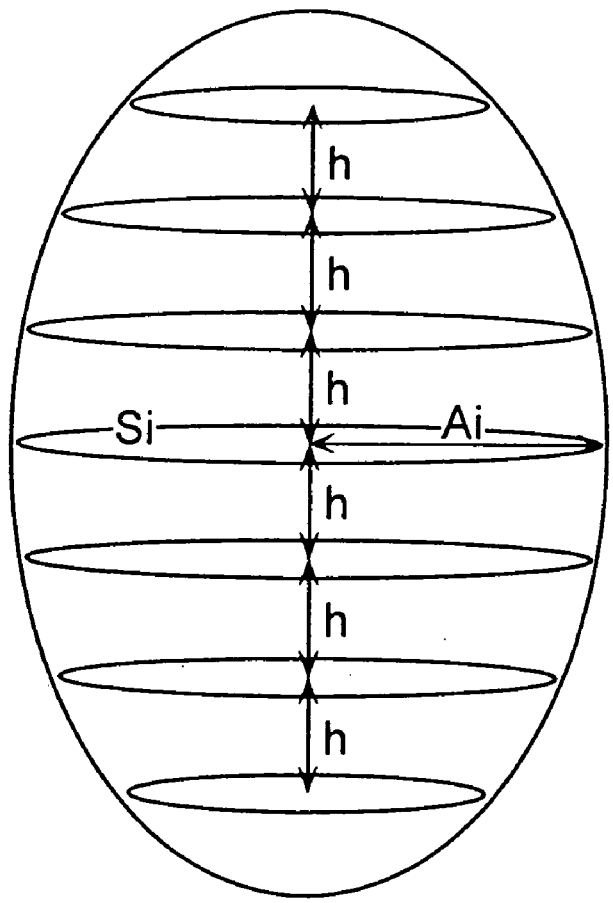
FIG. 26 is a diagram used to explain a modification method (Simpson method) for capacity calculation performed by the automatic capacity measuring unit.
Figure 27:
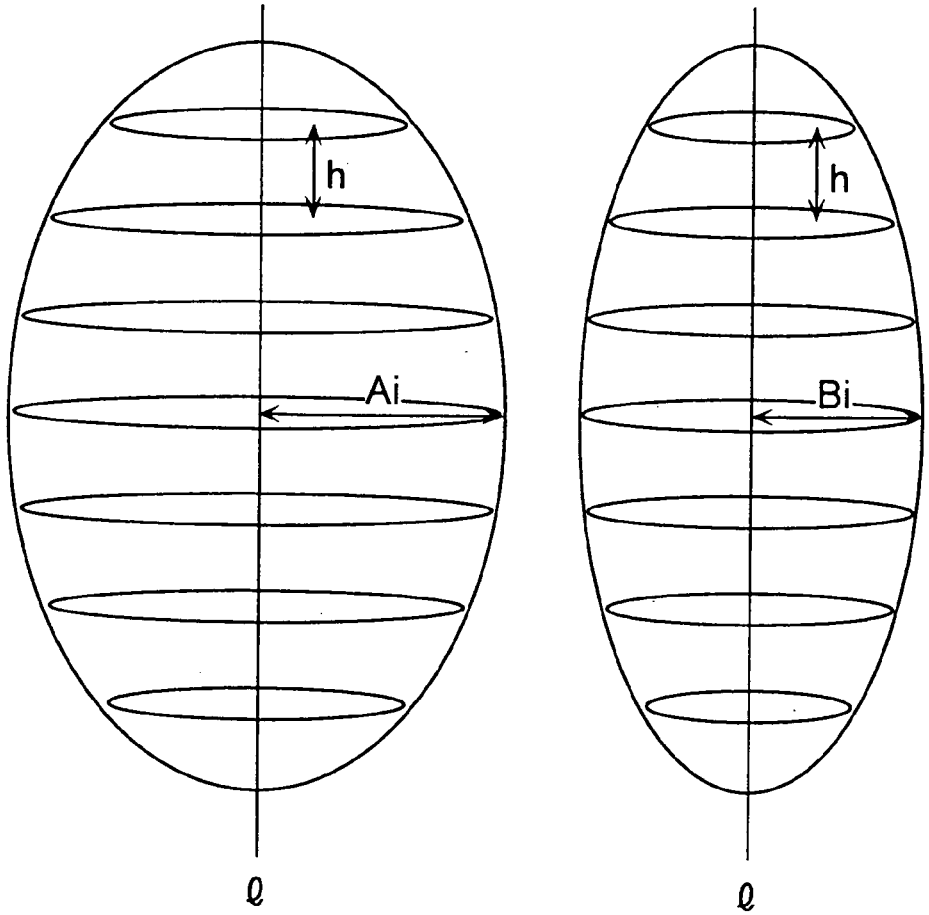
FIG. 27 is a diagram used to explain a modification method (modified Simpson method) for capacity calculation performed by the automatic capacity measuring unit.

For instance, when an ultrasound image for a cross section viewed from only one direction can be obtained, an approximate expression in accordance with the Simpson method may be used to calculate the object's capacity as shown in FIG. 26. When ultrasound images for different cross sections that are orthogonal to each other are obtained, an approximate expression under the modified Simpson method may be used, as shown in FIG. 27.

For these two approximate expressions, an object of interest is divided into a plurality of slices, and a radius "Ai" (and a radius "Bi") of each slice and a length "l" between two slices are used for calculation based on the shown approximate expressions to yield an approximate volume of the object. Although the present two approximate expressions do not achieve a real-time feature as achieved by the plane area length method of the above embodiment because they require a plurality of ultrasound images, they have an advantage of correctly calculating a capacity that is very close to the object's actual capacity.

The ultrasonic diagnostic devices of the present invention have been described based on several embodiments and example modifications. The present invention, however, is not limited to these embodiments and example modifications, and the following modifications are also possible.

Figure 28:
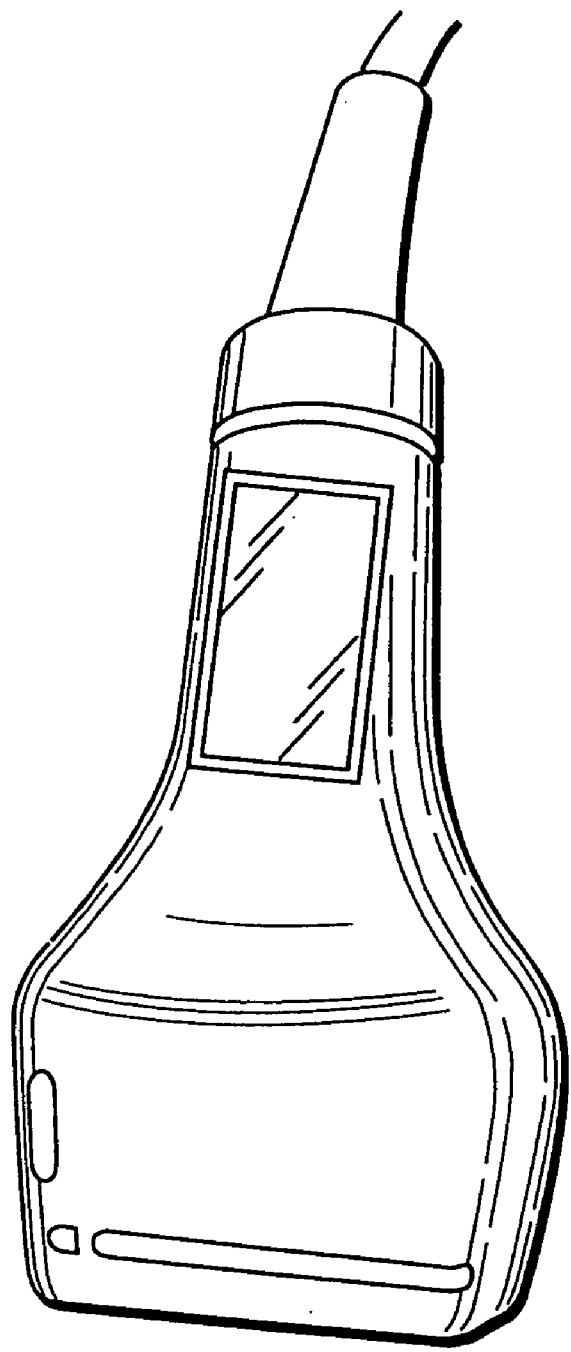
FIG. 28 is an external view of a probe of an example modification for which an LCD unit is provided in a handle part near a cable of the probe.

The probe 13 of the ultrasonic diagnostic device 10 may include the LCD unit in its handle part near the cable as shown in FIG. 28 or may not include any LCD unit as in ordinary probes although the probe 13 of the above embodiments includes the LCD unit in its top part on the back.

It is of course possible to combine given independent elements and units, which bear no exclusive relations with one another, of the above ultrasonic diagnostic devices so as to achieve an ultrasonic diagnostic device with a variety of functions and features. For instance, it is possible to combine the following units: the real time control unit 113 of the first embodiment for controlling a frame rate based on which an object's cross section viewed from a single direction is scanned; the pulsebeat synchronizing unit 130 of the second embodiment for combining different ultrasound images of cross sections viewed from a plurality of directions; the automatic contour extracting unit 220 of the above example modification for extracting the contour of the object with great accuracy; and the contour use ascertaining unit 321 of the example modification to determine whether or not contours for two cross sections that are orthogonal to each other are collectively processed. This combination achieves an ultrasonic diagnostic device which is capable of highly accurate contour extraction and capacity calculation that reflect the knowledge of the operator.

The ultrasonic diagnostic devices of the present invention do not reject an operator's input operation during diagnosis and can operate in accordance with an operator's instructions for a variety of operations.

Figure 29:
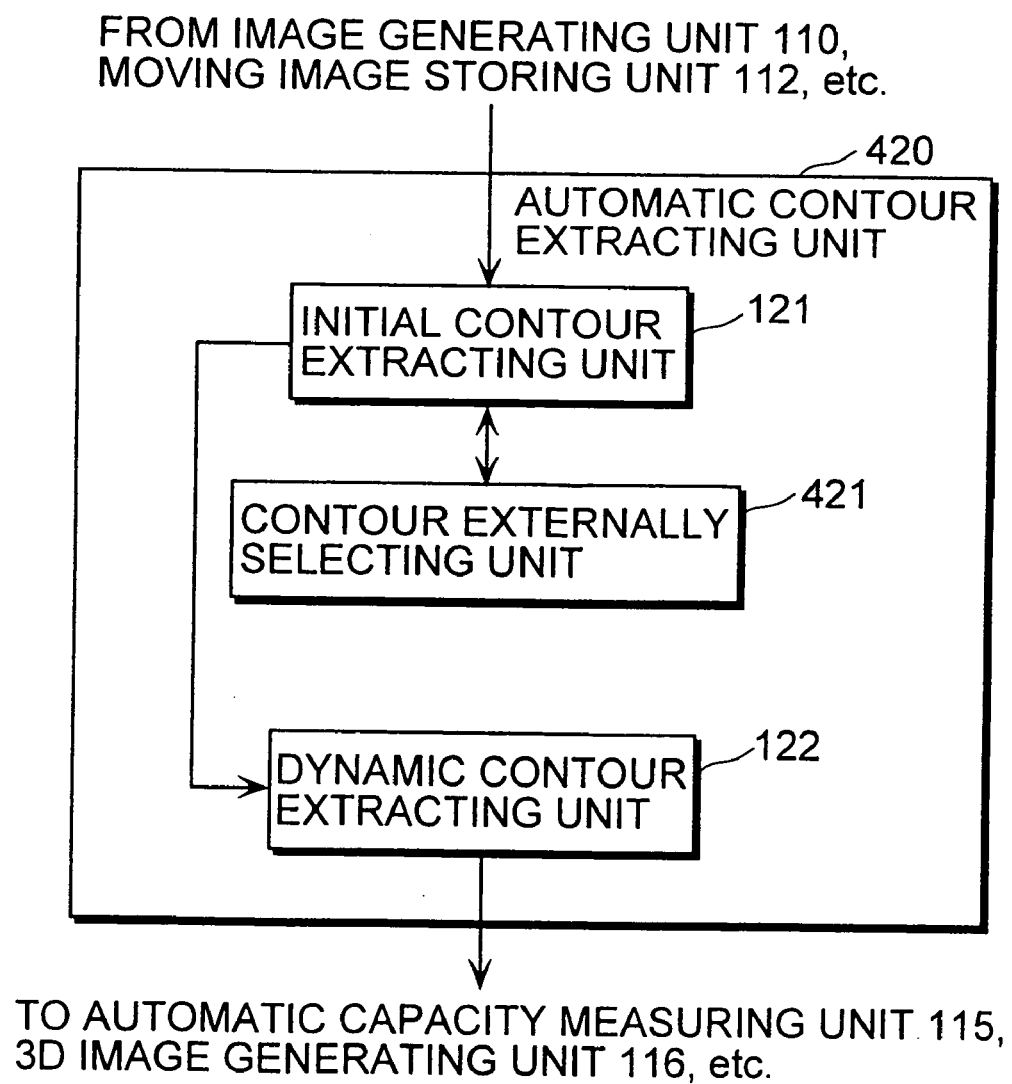
FIG. 29 is a block diagram showing a function configuration of an automatic contour extracting unit according to an example modification containing a contour externally selecting unit.

For instance, although the automatic contour extracting unit 220 shown in FIG. 19 automatically selects certain initial contours that are used for the subsequent operation from a plurality of candidate initial contours, it is alternatively possible, as in an automatic contour extracting unit 420 shown in FIG. 29, that the operator specifies, out of a plurality of contours extracted by an initial contour extracting unit 121, an initial contour for the subsequent use while viewing the display apparatus 11. For achieving this, a contour externally selecting unit 421 may be provided.

Figure 30:
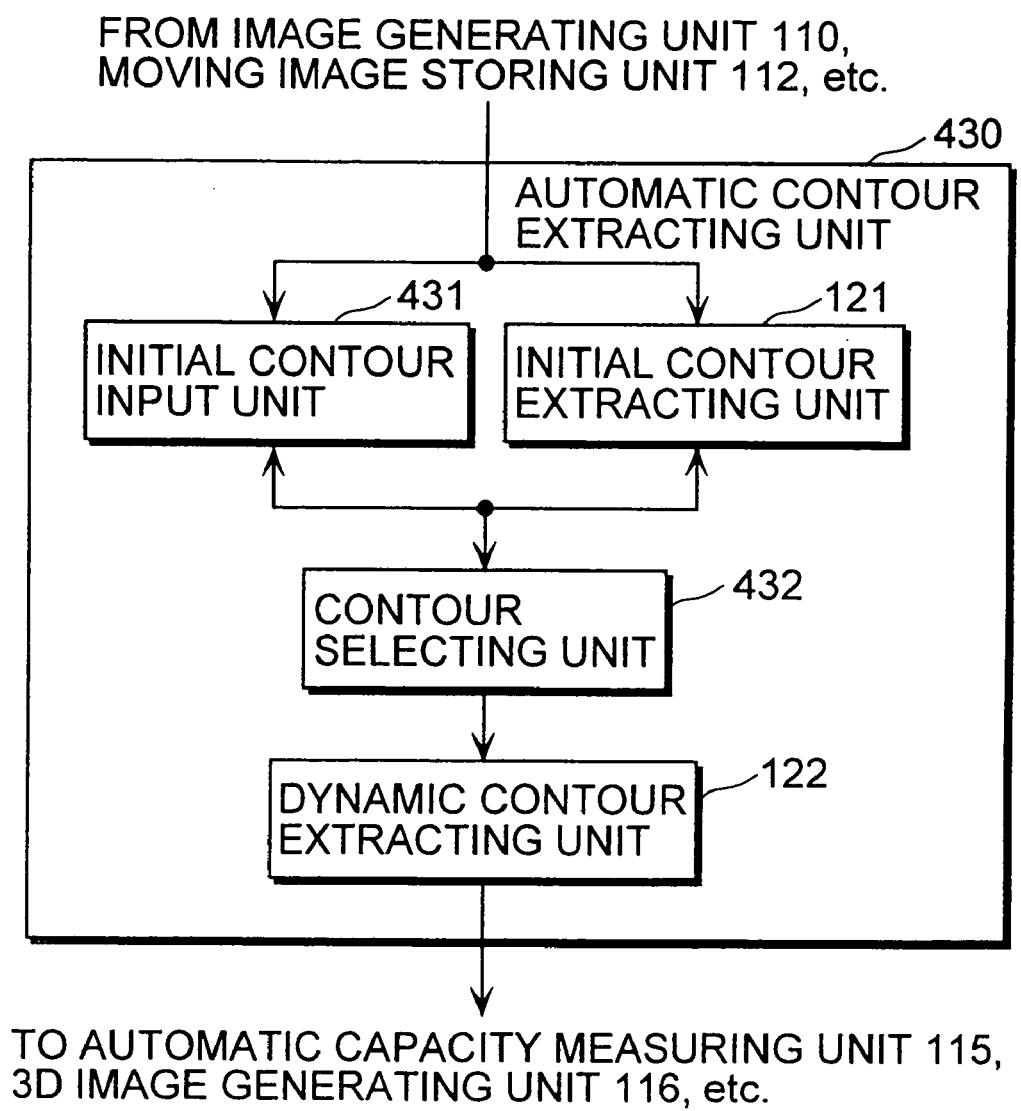
FIG. 30 is a block diagram showing a function configuration of an automatic contour extracting unit according to an example modification containing an initial contour input unit.

As shown in FIG. 30, it is alternatively possible to provide an automatic contour extracting unit 430 which includes the following units: an initial contour input unit 431 for obtaining and storing an initial contour in accordance with a dialog (interaction) with the operator; and a contour selecting unit 432 for selecting, in accordance with a parameter and the like that are set beforehand, either the stored initial contour or another initial contour that is automatically extracted by an initial contour extracting unit 121, and for sending the selected initial contour to a dynamic contour extracting unit 122.

Not that this operator's input operation is for specifying not a precise contour of an object but an initial contour of the object and that the operator's load of such operation is very small especially when types of target objects such as organs are limited. This modification may therefore reduce overall diagnosis time in some cases.

Similarly, although the contour correcting unit 114 of the above embodiments automatically corrects a contour in accordance with a stored standard in real time, the contour correcting unit 114 may perform, instead of such real-time automatic correction, correction on an accumulated ultrasound image while interacting with the operator.

The image normalizing unit 111 and the density adjusting unit 121a within the automatic contour extracting unit 120 of the above embodiments may be provided as a single unit because both of the units 111 and 121a perform image processing to improve the contrast of a region and an object that is subject to examination within an ultrasound image. For instance, an image normalizing unit may perform equalization for facilitating contour extraction, in addition to predetermined normalization for the entire ultrasound image.

The ultrasonic diagnostic devices of the above embodiments may limit the target object that is subject to examination to a left ventricle of a heart, a fetus, and the like. The ultrasonic diagnostic device of the second embodiment is particularly suitable for use dedicated to heart diagnosis since this diagnostic device is capable of extracting images synchronized by a pulsebeat from ultrasound images corresponding to two cross sections that are orthogonal to each other, and is capable of calculating a capacity of the object with high accuracy. For such a dedicated ultrasonic diagnostic device, parameters to be stored can be limited to those related to the left ventricle, and the processing can be simplified. This makes it possible to not only invest the system resource intensively in the processing related to the left ventricle and achieve higher-speed system performance but also reduce the cost by omitting unused functions. The user therefore benefits from the improved ease of use resulting from the enhanced system performance.

In the above example modifications shown in FIGS. 23–25, the method for extracting an initial contour based on the past extraction results is described by using three frames "A", "B", and "C." The number of such frames, however, is not limited to three and may be five, for example. In this case, five frames are used for equalization and interpolation to estimate an initial contour that comes midway between these frames in timing.

The processing of the automatic contour extracting units of the present ultrasonic diagnostic devices may be applied to more common images obtained by a digital camera and the like as well as to an ultrasound image obtained by an ultrasonic diagnostic device. Embodying such contour extraction function as a program and having this program executed by a computer such as a PC achieve a general-purpose image processing device having a contour extraction function according to the preset invention.

What is claimed is:

1. An ultrasonic diagnostic device that generates and displays an ultrasound image containing an object which is subject to examination in accordance with reflection of ultrasound, said ultrasonic diagnostic device comprising:
   an automatic contour extracting unit operable to extract a final contour of the object from the ultrasound image by performing a predetermined operation on the ultrasound image;
   an automatic capacity calculating unit operable to calculate a capacity of the object by using the final contour extracted by said automatic contour extracting unit; and
   a measurement display unit operable to display the capacity calculated by said automatic capacity calculating unit;
   wherein said automatic contour extracting unit includes:
      an initial contour extracting unit operable to roughly extract an initial contour of the object; and
      a dynamic contour extracting unit operable to accurately extract the final contour by using the initial contour extracted by said initial contour extracting unit as an initial value and by applying an active contour model to the object within the ultrasound image; and
   wherein said measurement displaying unit is operable to display the capacity while leaving previously calculated capacities displayed so as to display a transition of capacity over time.

2. The ultrasonic diagnostic device of claim 1, wherein:
   said automatic contour extracting unit is operable to extract a contour of a left ventricle of a heart as the final contour;
   said automatic capacity calculating unit is operable to calculate a capacity of the left ventricle; and
   said measurement displaying unit is operable to display the capacity of the left ventricle while leaving previously calculated capacities displayed to thereby display a transition of the capacity of the left ventricle over time.

3. An ultrasonic diagnostic device that generates and displays an ultrasound image containing an object which is subject to examination in accordance with reflection of ultrasound, said ultrasonic diagnostic device comprising:
   an automatic contour extracting unit operable to extract a final contour of the object from the ultrasound image by performing a predetermined operation on the ultrasound image;
   an automatic capacity calculating unit operable to calculate a capacity of the object by using the final contour extracted by said automatic contour extracting unit; and
   a real time control unit operable to have an operation repeatedly performed at a fixed frame rate, the operation including: (a) generation of the ultrasound image; (b) the extraction of the final contour by said automatic contour extracting unit; and (c) the calculation of the capacity of the object by said automatic capacity calculating unit;
   wherein said automatic contour extracting unit includes:
      an initial contour extracting unit operable to roughly extract an initial contour of the object; and
      a dynamic contour extracting unit operable to accurately extract the final contour by using the initial contour extracted by said initial contour extracting unit as an initial value and by applying an active contour model to the object within the ultrasound image; and
   wherein said real time control unit includes a frame rate control unit operable to monitor the operation and change the frame rate to have the operation completely performed.

4. An ultrasonic diagnostic device that generates and displays an ultrasound image containing an object which is subject to examination in accordance with reflection of ultrasound, said ultrasonic diagnostic device comprising:
   an automatic contour extracting unit operable to extract a final contour of the object from the ultrasound image by performing a predetermined operation on the ultrasound image;
   a contour correcting unit operable to correct the final contour extracted by said automatic contour extracting unit in accordance with either interaction with an operator or a standard that said contour correcting unit stores; and
   a use ascertaining unit operable to determine, for one of the extracted final contour and the corrected final contour, whether the final contour is used for subsequent operation in accordance with interaction with the operator;
   wherein said automatic contour extracting unit includes:
      an initial contour extracting unit operable to roughly extract an initial contour of the object; and
      a dynamic contour extracting unit operable to accurately extract the final contour by using the initial contour extracted by said initial contour extracting unit as an initial value and by applying an active contour model to the object within the ultrasound image.

5. The ultrasonic diagnostic device of claim 4, further comprising an automatic capacity calculating unit operable to calculate a capacity of the object by using the final contour determined to be used by said use ascertaining unit.

6. The ultrasonic diagnostic device of claim 5, further comprising a three-dimensional image generating unit operable to accumulate each final contour determined to be used so as to generate and display a three-dimensional image for the object.

7. An ultrasonic diagnostic device that generates and displays an ultrasound image containing an object which is subject to examination in accordance with reflection of ultrasound, said ultrasonic diagnostic device comprising:
   an automatic contour extracting unit operable to extract a final contour of the object from the ultrasound image by performing a predetermined operation on the ultrasound image; and
   an image normalizing unit operable to normalize the ultrasound image by converting a density of pixels of the ultrasound image in such a way as to make a density distribution of the ultrasound image satisfy a predetermined condition;
   wherein said automatic contour extracting unit includes:
      an initial contour extracting unit operable to roughly extract an initial contour of the object; and
      a dynamic contour extracting unit operable to accurately extract the final contour by using the initial contour extracted by said initial contour unit as an initial value and by applying an active contour model to the object within the ultrasound image;
   wherein said automatic contour extracting unit is operable to perform the predetermined operation on the normalized ultrasound image to extract the final contour; and wherein said image normalizing unit includes:
a condition storing unit operable to store the predetermined condition in advance;
a density converting unit operable to convert the density of the pixels by using a plurality of transform functions to generate a plurality of ultrasound images; and
a control judging unit operable to specify, out of the plurality of ultrasound images, an ultrasound image that satisfies the predetermined condition stored in said condition storing unit, and output the specified ultrasound image as a normalized ultrasound image.

8. An image processing device that extracts a final contour of an object that is subject to examination from an ultrasound image, said image processing device comprising:
an automatic contour extracting unit operable to extract the final contour;
an automatic capacity calculating unit operable to calculate a capacity of the object by using the final contour extracted by said automatic contour extracting unit; and
a measurement display unit operable to display the capacity calculated by said automatic capacity calculating unit;
wherein said automatic contour extracting unit includes:
an initial contour extracting unit operable to roughly extract an initial contour of the object; and
a dynamic contour extracting unit operable to accurately extract the final contour by using the initial contour extracted by said initial contour extracting unit as an initial value and by applying an active contour model to the object within the ultrasound image; and
wherein said measurement displaying unit is operable to display the capacity while leaving previously calculated capacities displayed to thereby display a transition of capacity over time.

9. A program stored on a computer-readable medium, said program causing a computer to execute operations comprising:
roughly extracting an initial contour of the object by performing a predetermined operation on the ultrasound image;
accurately extracting a final contour of the object by using the initial contour extracted in said roughly extracting of the initial contour as an initial value and by applying an active contour model to the object within the ultrasound image;
calculating a capacity of the object by using the final contour extracted in said accurately extracting of the final contour; and
displaying the capacity calculated in said calculating of the capacity while leaving previously calculated capacities displayed to thereby display a transition of capacity over time.

* * * * *